(12) United States Patent
Mercier et al.

(10) Patent No.: US 10,883,112 B2
(45) Date of Patent: Jan. 5, 2021

(54) PLANTS PRODUCING 2N GAMETES OR APOMEIOTIC GAMETES

(71) Applicant: INSTITUT NATIONAL DE LA RECHERCHE AGRONOMIQUE, Paris (FR)

(72) Inventors: Raphael Mercier, Fontenay-le-Fleury (FR); Isabelle D'Erfurth, Quetigny (FR); Nicole Froger, Saint-Cyr-l'Ecole (FR); Sylvie Jolivet, Bois d'Arcy (FR); Laurence Cromer, Clamart (FR)

(73) Assignee: Institut National de Recherche Pour l'Agriculture, l'Alimentation et l'Environnement, Paris (FR)

(*) Notice: Subject to any disclaimer, the term of this patent is extended or adjusted under 35 U.S.C. 154(b) by 589 days.

(21) Appl. No.: 15/006,847

(22) Filed: Jan. 26, 2016

(65) Prior Publication Data

US 2016/0222397 A1     Aug. 4, 2016

Related U.S. Application Data

(63) Continuation of application No. 13/143,530, filed as application No. PCT/IB2010/000184 on Jan. 6, 2010, now abandoned.

(30) Foreign Application Priority Data

Jan. 7, 2009   (EP) .................................... 09290010

(51) Int. Cl.
*C12N 15/82* (2006.01)
*C07K 14/415* (2006.01)

(52) U.S. Cl.
CPC ........ *C12N 15/8218* (2013.01); *C07K 14/415* (2013.01); *C12N 15/8287* (2013.01)

(58) Field of Classification Search
None
See application file for complete search history.

(56) References Cited

U.S. PATENT DOCUMENTS

2007/0044171 A1* 2/2007 Kovalic ................. A01G 22/00
800/278

OTHER PUBLICATIONS

Cromer et al. (PLoS genetics 8.7 (2012): e1002865). (Year: 2012).*
Uniprot Accession C0HF56, 2009. (Year: 2009).*
Vu et al. (Frontiers in plant science 8 (2017): 332). (Year: 2017).*
Hase et al. (46 Plant Journal, 317-326 (2006). (Year: 2006).*
D'Erfurth et al. (PLoS biology 7.6 (2009): e1000124). (Year: 2009).*
Kuromori et al. (The Plant Journal 37.6 (2004): 897-905). (Year: 2004).*
Helliwell et al. (Methods in enzymology. vol. 392. Academic Press, 2005. 24-35). (Year: 2005).*
GenBank Accession NM115648 dated Jun. 6, 2006. (Year: 2006).*
GenBank Accession NM 129788 dated Aug. 20, 2002. (Year: 2002).*

* cited by examiner

*Primary Examiner* — Charles Logsdon
(74) *Attorney, Agent, or Firm* — Morgan, Lewis & Bockius LLP

(57) ABSTRACT

The invention relates to plants wherein the protein OSD1, involved in the transition from meiosis I to meiosis II is inactive. These plants produce Second Division Restitution (SDR) 2n gametes. The invention further relates to plants wherein the inactivation of OSD1 is combined with the inactivation of a gene involved in meiotic recombination in plants, and of a gene involved in the monopolar orientation of the kinetochores during meiosis. These plants produce apomeiotic gametes. These plants are useful in plant breeding.

13 Claims, 7 Drawing Sheets

Specification includes a Sequence Listing.

PLANTS PRODUCING 2N GAMETES OR APOMEIOTIC GAMETES

CROSS-REFERENCE TO RELATED APPLICATIONS

This application is continuation of U.S. application Ser. No. 13/143,530, filed Sep. 16, 2011, which in turn is a U.S. National Stage application of international application PCT/I132010/000184, filed in English on Jan. 6, 2010, which designates the United States, and which claims of priority to EP 09290010.9, filed in English on Jan. 7, 2009. Each of these applications is incorporated by reference herein in its entirety.

BACKGROUND

The invention relates to plants that produce 2n Second Division Restitution (SDR) gametes, and to plants that produce apomeiotic gametes, and to their use in plant breeding.

2n gametes (also known as diplogametes) are gametes having the somatic chromosome number rather than the gametophytic chromosome number. They have been shown to be useful for the genetic improvement of several crops (for review, cf. for instance RAMANNA & JACOBSEN, Euphytica 133, 3-18, 2003). In particular, the production of diplogametes allow crosses between plants of different ploidy level, for instance crosses between tetraploid crop plants and their diploid wild relatives, in order to use their genetic diversity in plant breeding programs.

The formation of 2n gametes results from anomalies during meiosis (for review cf. VEILLEUX, Plant Breeding Reviews 3, 252-288, 1985, or BRETAGNOLLE & THOMPSON, New Phytologist 129, 1-22, 1995).

In normal meiosis, chromosomes first duplicate, resulting in pairs of sister chromatids. This round of replication is followed by two rounds of division, known as meiosis I and meiosis II. During meiosis I homologous chromosomes recombine and are separated into two cells, each of them comprising one entire haploid content of chromosomes. In meiosis II the two cells resulting from meiosis I further divide, and the sister chromatids segregate. The spores resulting from this division are thus haploid and carry recombined genetic information.

The abnormalities leading to 2n gametes formation include in particular abnormal cytokinesis, the skip of the first or second meiotic division, or abnormal spindle geometry (for review cf. VEILLEUX, Plant Breeding Reviews 3, 252-288, 1985, or BRETAGNOLLE & THOMPSON, New Phytologist 129, 1-22, 1995). These abnormalities lead to different classes of unreduced gametes. For instance, failure of the first meiotic division results in First Division Restitution (FDR) gametes, while failure of the second meiotic division results in Second Division Restitution (SDR) gametes.

Although numerous mutants able to produce 2n gametes have been reported in various plant species, only one gene implicated in the formation of 2n pollen has been identified and characterized at the molecular level until now. The inactivation of this gene, designated AtPS1 (for *Arabidopsis thaliana* parallel spindles), generates diploid male spores, giving rise to viable diploid pollen grains and to spontaneous triploid plants in the progeny. This gene and its use for producing 2n pollen are disclosed in European Patent application 08490672, filed on Jul. 8, 2008, and in the publication of D'ERFURTH et al (PLoS Genet. 2008 November; 4(11): e1000274. Epub 2008 Nov. 28).

SUMMARY

The inventors have now identified in the model plant *Arabidopsis thaliana*, another gene implicated in the formation of 2n gametes in plants. The inventors have found that inactivation of this gene results in the skipping of the second meiotic division. This generates diploid male and female spores, giving rise to viable diploid male and female gametes, which are SDR gametes. This gene will be hereinafter designated OSD1, for omission of second division. The sequence of the OSD1 gene of *Arabidopsis thaliana* is available in the TAIR database under the accession number At3g57860, or in the GenBank database under the accession number NM_115648. This gene encodes a protein of 243 aa (GenBank NP_191345), whose sequence is also represented in the enclosed sequence listing as SEQ ID NO: 1.

The OSD1 gene of *Arabidopsis thaliana* has been previously depicted as "UVI4-Like" gene (UVI4-L), in a publication of HASE et al. (Plant J, 46, 317-26, 2006), which describes its paralogue, named UVI4. According to HASE et al. UVI4 acts as a suppressor of endo-reduplication and is necessary for maintaining the mitotic state whereas OSD1 (UVI4-L) does not appear to be required for this process. In contrast, as shown herein, OSD1 appears necessary for allowing the transition from meiosis I to meiosis II.

The inventors have also identified in rice (*Oryza sativa*) an ortholog of the OSD1 gene of *Arabidopsis thaliana*. The sequence of the OSD1 gene of *Oryza sativa* is available in the OryGenes or TAIR databases under the accession number Os02g37850. It encodes a protein of 234 aa, whose sequence is represented in the enclosed sequence listing as SEQ ID NO: 35. The OSD1 proteins of *Arabidopsis thaliana* and *Oryza sativa* have 23.6% identity and 35% similarity over the whole length of their sequences.

The invention thus provides a method for obtaining a plant producing Second Division Restitution 2n gametes, wherein said method comprises the inhibition in said plant of a protein hereinafter designated as OSD1 protein, wherein said protein has at least 20%, and by order of increasing preference, at least 25, 30, 35, 40, 45, 50, 55, 60, 65, 70, 75, 80, 85, 90, 95 or 98% sequence identity, or at least 29%, and by order of increasing preference, at least 35, 40, 45, 50, 55, 60, 65, 70, 75, 80, 85, 90, 95 or 98% sequence similarity with the AtOSD1 protein of SEQ ID NO: 1 or with the OsOSD1 protein of SEQ ID NO: 35.

DETAILED DESCRIPTION

Unless otherwise specified, the protein sequence identity and similarity values provided herein are calculated over the whole length of the sequences, using the BLASTP program under default parameters, or the Needleman-Wunsch global alignment algorithm (EMBOSS pairwise alignment Needle tool under default parameters). Similarity calculations are performed using the scoring matrix BLOSUM62.

The SDR 2n gametes produced according to the invention are useful in all the usual applications of 2n gametes, for instance for producing polyploids plants, or to allow crosses between plants of different ploidy level. They can also be useful in methods of genetic mapping, for instance the method of "Reverse progeny mapping" disclosed in US Patent Application 20080057583.

The inventors have further found that by combining the inactivation of OSD1, with the inactivation of two other genes, one (SPO11-1) which encodes a protein necessary for efficient meiotic recombination in plants, and whose inhibition eliminates recombination and pairing (GRELON et al., Embo J, 20, 589-600, 2001), and another (REC8, At2g47980) which encodes a protein necessary for the monopolar orientation of the kinetochores during meiosis (CHELYSHEVA et al., J Cell Sci, 118, 4621-32, 2005), and whose inhibition modifies chromatid segregation, resulted in a genotype in which meiosis is totally replaced by mitosis without affecting subsequent sexual processes. This genotype will be called hereinafter MiMe for "mitosis instead of meiosis". This replacement of meiosis by mitosis results in apomeiotic gametes, retaining all the parent's genetic information (BICKNELL & KOLTUNOW, Plant Cell, 16 Suppl, S228-45, 2004).

Figure 1:
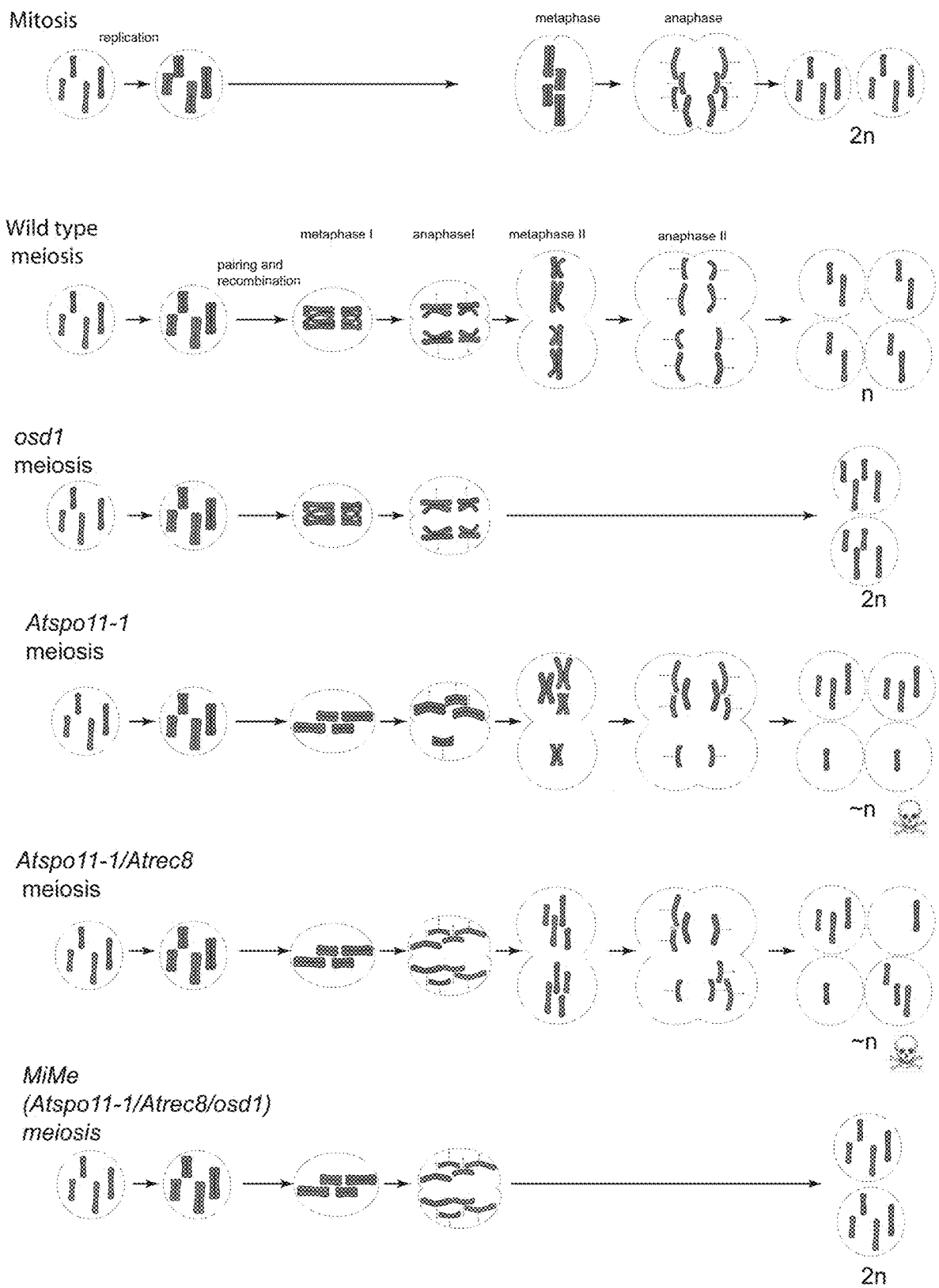
FIG. 1 provides a schematic comparison between the mechanisms of mitosis, normal meiosis, meiosis in the osd1 mutant, meiosis in a mutant lacking SPO11-1 activity (Atspo11-1), meiosis in a double mutant lacking both SPO11-1 and REC8 activity (Atspo11-1/Atrec8), and meiosis in the MiMe mutant.

FIG. 1 provides a schematic comparison between the mechanisms of mitosis, normal meiosis, meiosis in the osd1 mutant, meiosis in a mutant lacking SPO11-1 activity (Atspo11-1), meiosis in a double mutant lacking both SPO11-1 and REC8 activity (Atspo11-1/Atrec8), and meiosis in the MiMe mutant.

During mitosis in diploid cells, chromosomes replicate and sister chromatids segregate to generate daughter cells that are diploid and genetically identical to the initial cell. During normal meiosis, two rounds of chromosome segregation follow a single round of replication. At division one, homologous chromosomes recombine and are separated. Meiosis II is more similar to mitosis resulting in equal distribution of sister chromatids. The obtained spores are thus haploid and carry recombined genetic information. In the osd1 mutant (this study) meiosis II is skipped giving rise to diploid spores and SDR gametes with recombined genetic information.

The Atspo11-1 mutant undergoes an unbalanced first division followed by a second division leading to unbalanced spores and sterility.

The Atspo11-1/Atrec8 double mutant undergoes a mitotic-like division instead of a normal first meiotic division, followed by an unbalanced second division leading to unbalanced spores and sterility.

In the triple osd1/Atspo11-1/Atrec8 mutant (MiMe), the presence of the Atspo11-1 and Atrec8 mutations leads to a mitotic-like first meiotic division and the presence of the osd1 mutation prevents the second meiotic division from occurring. Thus meiosis is replaced by a mitotic-like division. The obtained spores and gametes are genetically identical to the initial cell.

The apomeiotic gametes produced by the MiMe mutant can be used, in the same way as the SDR 2n gametes, for producing polyploids plants, or for crossing plants of different ploidy level. They are also of interest for the production of apomictic plants, i.e plants which are able to form seeds from the maternal tissues of the ovule, resulting in progeny that are genetic clones of the maternal parent. Although it exists in over 400 species of angiosperms, very few crop species are apomictic and attempts to introduce this trait by crossing have failed (SAVIDAN, The Flowering of Apomixis: From Mechanisms to Genetic Engineering 2001; SPILLANE et al., Sexual Plant Reproduction, 14, 2001).

A further object of the present invention is thus a method for obtaining a plant producing apomeiotic gametes, wherein said method comprises the inhibition in said plant of the following proteins:

a) an OSD1 protein as defined above;

b) a protein involved in initiation of meiotic recombination in plants, said protein being selected among:

i) a protein hereinafter designated as SPO11-1 protein, wherein said protein has at least 40%, and by order of increasing preference, at least 45, 50, 55, 60, 65, 70, 75, 80, 85, 90, 95 or 98% sequence identity, or at least 60%, and by order of increasing preference, at least, 65, 70, 75, 80, 85, 90, 95 or 98% sequence similarity with the SPO11-1 protein of SEQ ID NO: 2;

ii) a protein hereinafter designated as SPO11-2 protein, wherein said protein has at least 40%, and by order of increasing preference, at least 45, 50, 55, 60, 65, 70, 75, 80, 85, 90, 95 or 98% sequence identity, or at least 60%, and by order of increasing preference, at least, 65, 70, 75, 80, 85, 90, 95 or 98% sequence similarity with the SPO11-2 protein of SEQ ID NO: 3;

iii) a protein hereinafter designated as PRD1 protein, wherein said protein has at least 25%, and by order of increasing preference, at least 30, 35, 40, 45, 50, 55, 60, 65, 70, 75, 80, 85, 90, 95 or 98% sequence identity, or at least 35%, and by order of increasing preference, at least, 40, 45, 50, 55, 60, 65, 70, 75, 80, 85, 90, 95 or 98% sequence similarity with the PRD1 protein of SEQ ID NO: 4;

iv) a protein hereinafter designated as PAIR1 protein, wherein said protein has at least 30%, and by order of increasing preference, at least 35, 40, 45, 50, 55, 60, 65, 70, 75, 80, 85, 90, 95 or 98% sequence identity, or at least 40%, and by order of increasing preference, at least, 45, 50, 55, 60, 65, 70, 75, 80, 85, 90, 95 or 98% sequence similarity with the PAIR1 protein of SEQ ID NO: 5;

c) a protein hereinafter designated as Rec8 protein, wherein said protein has at least 40%, and by order of increasing preference, at least 45, 50, 55, 60, 65, 70, 75, 80, 85, 90, 95 or 98% sequence identity, or at least 45%, and by order of increasing preference, at least, 50, 55, 60, 65, 70, 75, 80, 85, 90, 95 or 98% sequence similarity with the Rec8 protein of SEQ ID NO: 6.

SEQ ID NO: 2 represents the sequence of the SPO11-1 protein of *Arabidopsis thaliana*. This sequence is also available in the Swissprot database under the accession number Q9M4A2.

SEQ ID NO: 3 represents the sequence of the SPO11-2 protein of *Arabidopsis thaliana*. This sequence is also available in the SwissProt database under the accession number Q9M4A1.

SEQ ID NO: 4 represents the sequence of the PRD1 protein of *Arabidopsis thaliana*. This sequence is also available in the GenBank database under the accession number ABQ12642.

SEQ ID NO: 5 represents the sequence of the PAIR1 protein of *Arabidopsis thaliana*. This sequence is also available in the GenBank database under the accession number NP_171675.

SEQ ID NO: 6 represents the sequence of the Rec8 protein of *Arabidopsis thaliana*. This sequence is also available in the GenBank database under the accession number NP_196168.

The SPO11-1, SPO11-2, PRD1, PAIR1, and Rec8 proteins are conserved in higher plants, monocotyledons as well as dicotyledons. By way of non-limitative examples of orthologs of SPO11-1, SPO11-2, PRD1, PAIR1 and Rec8 proteins of *Arabidopsis thaliana* in monocotyledonous plants, one can cite the *Oryza sativa* SPO11-1, SPO11-2, PRD1, PAIR1, and Rec8 proteins. The sequence of the *Oryza sativa* SPO11-1 protein is available in GenBank under the accession number AAP68363; the sequence of the *Oryza sativa* SPO11-2 protein is available in GenBank under the accession number NP_001061027; the sequence of the *Oryza sativa* PRD1 protein is available in GenBank under the accession number EAZ30311; the sequence of the *Oryza sativa* PAIR1 protein is available in SwissProt under the accession number Q75RY2; the sequence of the *Oryza sativa* Rec8 protein is available in GenBank under the accession number AAQ75095.

The inhibition of the above mentioned OSD1, SPO11-1, SPO11-2, PRD1, PAIR1, or Rec8 proteins can be obtained either by abolishing, blocking, or decreasing their function, or advantageously, by preventing or down-regulating the expression of the corresponding genes.

By way of example, inhibition of said protein can be obtained by mutagenesis of the corresponding gene or of its promoter, and selection of the mutants having partially or totally lost the activity of said protein. For instance, a mutation within the coding sequence can induce, depending on the nature of the mutation, the expression of an inactive protein, or of a protein with impaired activity; in the same way, a mutation within the promoter sequence can induce a lack of expression of said protein, or decrease thereof.

Mutagenesis can be performed for instance by targeted deletion of the coding sequence or of the promoter of the gene encoding said protein or of a portion thereof, or by targeted insertion of an exogenous sequence within said coding sequence or said promoter. It can also be performed by inducing random mutations, for instance through EMS mutagenesis or random insertional mutagenesis, followed by screening of the mutants within the desired gene. Methods for high throughput mutagenesis and screening are available in the art. By way of example, one can mention TILLING (Targeting Induced Local Lesions IN Genomes, described by McCallum et al., 2000).

Among the mutations within the OSD1 gene, those resulting in the ability to produce SDR 2n gametes can be identified on the basis of the phenotypic characteristics of the plants which are homozygous for this mutation: these plants can form at least 5%, preferably at least 10%, more preferably at least 20%, still more preferably at least 50%, and up to 100% of dyads as a product of meiosis.

Among the mutations within a gene encoding a protein involved in initiation of meiotic recombination in plants, such as the SPO11-1 gene or the SPO11-2, PRD1, or PAIR1 gene, those useful for obtaining a plant producing apomeiotic gametes can be identified on the basis of the phenotypic characteristics of the plants which are homozygous for this mutation, in particular the presence of univalents instead of bivalents at meiosis I, and the sterility of the plant.

Among the mutants having a mutation within the REC8 gene, those useful for obtaining a plant producing apomeiotic gametes can be identified on the basis of the phenotypic characteristics of the plants which are homozygous for this mutation, in particular chromosome fragmentation at meiosis, and sterility of the plant.

According to a preferred embodiment of the method of the invention for obtaining a plant able to produce SDR 2n gametes, said method comprises:

a) providing a plant having a mutation within an allele of the OSD1 gene resulting in the inhibition of the protein encoded by this allele, said plant being heterozygous for this mutation;

b) self fertilizing said plant of step a) in order to obtain a plant homozygous for said mutation.

According to a preferred embodiment of the method of the invention for obtaining a plant able to produce apomeiotic gametes, said method comprises:

a) providing a plant having a mutation within an allele of the OSD1 gene resulting in the inhibition of the protein encoded by this allele, said plant being heterozygous for this mutation;

b) providing a plant having a mutation within an allele of a gene selected among the SPO11-1, SPO11-2, PRD1, or PAIR1 gene resulting in the inhibition of the protein encoded by said allele, said plant being heterozygous for this mutation;

c) providing a plant having a mutation within an allele of the REC8 gene resulting in the inhibition of the protein encoded by said allele, said plant being heterozygous for this mutation;

e) crossing the plants of steps a) b) and c) in order to obtain a plant having a mutation within an allele of the OSD1 gene, a mutation within an allele of a gene selected among the SPO11-1, SPO11-2, PRD1, or PAIR1 gene, and a mutation within an allele of the REC8 gene, said plant being heterozygous for each mutation;

f) self fertilizing the plant of step e) in order to obtain a plant homozygous for the mutation within the OSD1 gene, for the mutation within the gene selected among the SPO11-1, SPO11-2, PRD1, or PAIR1 gene, and for the mutation within the REC8 gene.

Alternatively, the inhibition of the target protein is obtained by silencing of the corresponding gene. Methods for gene silencing in plants are known in themselves in the art. For instance, one can mention by antisense inhibition or co-suppression, as described by way of example in U.S. Pat. Nos. 5,190,065 and 5,283,323. It is also possible to use ribozymes targeting the mRNA of said protein.

Preferred methods are those wherein gene silencing is induced by means of RNA interference (RNAi), using a silencing RNA targeting the gene to be silenced. Various methods and DNA constructs for delivery of silencing RNAs are available in the art.

A "silencing RNA" is herein defined as a small RNA that can silence a target gene in a sequence-specific manner by base pairing to complementary mRNA molecules. Silencing RNAs include in particular small interfering RNAs (siRNAs) and microRNAs (miRNAs).

Initially, DNA constructs for delivering a silencing RNA in a plant included a fragment of 300 bp or more (generally 300-800 bp, although shorter sequences may sometime induce efficient silencing) of the cDNA of the target gene, under transcriptional control of a promoter active in said plant. Currently, the more widely used silencing RNA constructs are those that can produce hairpin RNA (hpRNA) transcripts. In these constructs, the fragment of the target gene is inversely repeated, with generally a spacer region between the repeats (for review, cf. WATSON et al., 2005). One can also use artificial microRNAs (amiRNAs) directed against the gene to be silenced (for review about the design and applications of silencing RNAs, including in particular amiRNAs, in plants cf. for instance OSSOWSKI et al., (Plant J., 53, 674-90, 2008).

The present invention provides tools for silencing one or more target gene(s) selected among OSD1, SPO11-1, SPO11-2, PRD1, PAIR1 and REC8, including in particular expression cassettes for hpRNA or amiRNA targeting said gene (s).

An expression cassette of the invention may comprise for instance:
a promoter functional in a plant cell;
one or more DNA construct(s) of 200 to 1000 bp, preferably of 300 to 900 bp, each comprising a fragment of a cDNA of a target gene selected among OSD1, SPO11-1, SPO11-2, PRD1, PAIR1, and REC8, or of its complementary, or having at least 95% identity, and by order of increasing preference, at least 96%, 97%, 98%, or 99% identity with said fragment, said DNA construct (s) being placed under transcriptional control of said promoter.

According to a preferred embodiment of the invention, an expression cassette for hpRNA comprises:
a promoter functional in a plant cell,
one or more hairpin DNA construct(s) capable, when transcribed, of forming a hairpin RNA targeting a gene selected among OSD1, SPO11-1, SPO11-2, PRD1, PAIR1, and REC8;
said DNA construct(s) being placed under transcriptional control of said promoter.

Generally, said hairpin DNA construct comprises: i) a first DNA sequence of 200 to 1000 bp, preferably of 300 to 900 bp, consisting of a fragment of a cDNA of the target gene, or having at least 95% identity, and by order of increasing preference, at least 96%, 97%, 98%, or 99% identity with said fragment; ii) a second DNA sequence that is the complementary of said first DNA, said first and second sequences being in opposite orientations and ii) a spacer sequence separating said first and second sequence, such that these first and second DNA sequences are capable, when transcribed, of forming a single double-stranded RNA molecule. The spacer can be a random fragment of DNA. However, preferably, one will use an intron which is spliceable by the target plant cell. Its size is generally 400 to 2000 nucleotides in length.

According to another preferred embodiment of the invention, an expression cassette for an amiRNA comprises:
a promoter functional in a plant cell,
one or more DNA construct(s) capable, when transcribed, of forming an amiRNA targeting a gene selected among OSD1, SPO11-1, SPO11-2, PRD1, PAIR1, and REC8;
said DNA construct(s) being placed under transcriptional control of said promoter.

Advantageously, an expression cassette of the invention comprises a DNA construct targeting the OSD1 gene. According to a particularly preferred embodiment it comprises: a DNA construct targeting the OSD1 gene, a DNA construct targeting a gene selected among, SPO11-1, SPO11-2, PRD1, and PAIR1, and a DNA construct targeting REC8.

A large choice of promoters suitable for expression of heterologous genes in plants is available in the art.

They can be obtained for instance from plants, plant viruses, or bacteria such as *Agrobacterium*. They include constitutive promoters, i.e. promoters which are active in most tissues and cells and under most environmental conditions, as well as tissue-specific or cell-specific promoters which are active only or mainly in certain tissues or certain cell types, and inducible promoters that are activated by physical or chemical stimuli, such as those resulting from nematode infection.

Non-limitative examples of constitutive promoters that are commonly used in plant cells are the cauliflower mosaic virus (CaMV) 35S promoter, the Nos promoter, the rubisco promoter, the Cassava vein Mosaic Virus (CsVMV) promoter.

Organ or tissue specific promoters that can be used in the present invention include in particular promoters able to confer meiosis-associated expression, such as the DMC1 promoter (KLIMYUK & JONES, Plant J, 11, 1-14, 1997); one can also use any of the the endogenous promoters of the genes OSD1, SPO11-1, SPO11-2, PRD1, PAIR1, or REC8.

The DNA constructs of the invention generally also include a transcriptional terminator (for instance the 35S transcriptional terminator, or the nopaline synthase (Nos) transcriptional terminator).

The invention also includes recombinant vectors containing a chimeric DNA construct of the invention. Classically, said recombinant vectors also include one or more marker genes, which allow for selection of transformed hosts.

The selection of suitable vectors and the methods for inserting DNA constructs therein are well known to persons of ordinary skill in the art. The choice of the vector depends on the intended host and on the intended method of transformation of said host. A variety of methods for genetic transformation of plant cells or plants are available in the art for many plant species, dicotyledons or monocotyledons. By way of non-limitative examples, one can mention virus mediated transformation, transformation by microinjection, by electroporation, microprojectile mediated transformation, *Agrobacterium* mediated transformation, and the like.

The invention also provides a host cell comprising a recombinant DNA construct of the invention. Said host cell can be a prokaryotic cell, for instance an *Agrobacterium* cell, or a eukaryotic cell, for instance a plant cell genetically transformed by a DNA construct of the invention. The construct may be transiently expressed; it can also be incorporated in a stable extrachromosomal replicon, or integrated in the chromosome.

According to a preferred embodiment of the method of the invention for providing a plant able to produce SDR 2n gametes, said plant is a transgenic plant, and said method comprises:

a) transforming at least one plant cell with a vector containing a DNA construct of the invention targeting the OSD1 gene;

b) cultivating said transformed plant cell in order to regenerate a plant having in its genome a transgene containing said DNA construct.

According to a preferred embodiment of the method of the invention for obtaining a plant able to produce apomeiotic gametes, said plant is a transgenic plant, and said method comprises:

a) transforming at least one plant cell with a vector containing a DNA construct of the invention targeting the OSD1 gene, a vector containing a DNA construct of the invention targeting a gene selected among SPO11-1, SPO11-2, PRD1, and PAIR1, and a vector containing a DNA construct of the invention targeting the REC8 gene;

b) cultivating said transformed plant cell in order to regenerate a plant having in its genome transgenes containing said DNA constructs.

According to another preferred embodiment of the method of the invention for obtaining a plant able to produce apomeiotic gametes, said plant is a transgenic plant, and said method comprises:

a) transforming at least one plant cell with a vector containing a DNA construct of the invention targeting the OSD1 gene, a DNA construct of the invention targeting a gene selected among SPO11-1, SPO11-2, PRD1, and PAIR1, and a vector containing a DNA construct of the invention targeting the REC8 gene;

b) cultivating said transformed plant cell in order to regenerate a plant having in its genome a transgene containing said DNA constructs.

The invention also encompasses plants able to produce SDR 2n gametes or apomeiotic gametes, obtainable by the methods of the invention.

This includes in particular plants comprising:
- a mutation within the OSD1 gene, wherein the OSD1 protein is inhibited as a result of this mutation; and
- a mutation within a gene selected among SPO11-1, SPO11-2, PRD1, or PAIR1 gene, wherein the SP011-1, SPO11-2, PRD1, or PAIR1 protein encoded by said gene is inhibited as a result of this mutation; and
- a mutation within the REC8 gene, wherein the Rec8 protein is inhibited as a result of this mutation.

This also includes plants genetically transformed by one or more DNA construct(s) of the invention. Preferably, said plants are transgenic plants, wherein said construct is contained in a transgene integrated in the plant genome, so that it is passed onto successive plant generations.

The expression of a chimeric DNA construct targeting the OSD1 gene, resulting in a down regulation of the OSD1 protein, provides to said transgenic plant the ability to produce 2n SDR gametes. The co-expression of a chimeric DNA construct targeting the OSD1 gene, a chimeric DNA construct targeting a gene selected among SPO11-1, SPO11-2, PRD1, and PAIR1, and a chimeric DNA construct targeting the REC8 gene, results in a down regulation of the proteins encoded by these three genes and provides to said transgenic plant the ability to produce apomeiotic gametes.

The invention also encompasses a method for producing SDR 2n gametes, wherein said method comprises cultivating a plant obtainable by a method of the invention and recovering the gametes produced by said plant. Preferably said gametes comprises at least 10%, more preferably at least 20%, and by order of increasing preference, at least 30%, 40%, 50%, 60%, 70%, 80%, or 90% of viable 2n gametes.

The invention also encompasses a method for producing apomeiotic gametes, wherein said method comprises cultivating a plant obtainable by a method of the invention and recovering the gametes produced by said plant. Preferably said gametes comprises at least 10%, more preferably at least 20%, and by order of increasing preference, at least 30%, 40%, 50%, or 60%, 70%, 80%, or 90% of viable apomeiotic gametes.

The present invention applies to a broad range of mono-cot- or dicotyledon plants of agronomical interest. By way of non-limitative examples, one can mention potato, rice, wheat, maize, tomato, cucumbers, alfafa, sugar cane, sweet potato, manioc, clover, soybean, ray-grass, banana, melon, watermelon, cotton or ornamental plants such as roses, lilies, tulips, and *narcissus*.

Foregoing and other objects and advantages of the invention will become more apparent from the following detailed description and accompanying drawings. It is to be understood however that this foregoing detailed description is exemplary only and is not restrictive of the invention.

EXAMPLES

Experimental Procedures

Plant Material and Growth Conditions

*Arabidopsis* plants were cultivated as described in VIGNARD et al., (PLoS Genet, 3, 1894-906, 2007). For germination assays and cytometry experiments *Arabidopsis* were cultivated in vitro on *Arabidopsis* medium (ESTELLE & SOMERVILLE, Mol. Gen. Genet., 206, 200-06, 1987) at 21° C. with a 16 h day/8 h night photoperiod and 70% hygrometry.

Genetic Analysis.

Plants were genotyped by PCR (30 cycles of 30 s at 94° C., 30 s at 56° C. and 1 min at 72° C.) using two primer pairs. For each genotype the primer pair is shown in Table I and the primer pair specific to the insertion is shown in Table II.

TABLE I

| | Primers for Wild-type allele |
|---|---|
| osd1-1 | pst15307U (5'CGTCACTCTCCCCAAGAAAG 3') (SEQ ID NO: 7) pst15307L (5'GGCTAAGCAAGCCTGCTATG 3') (SEQ ID NO: 8) |
| osd1-2 | GT21481U (5'CCGGTGTTCTTGTGACTCG 3') (SEQ ID NO: 9) GT21481L (5'GCAGATTCCTAATTCAGCTC 3') (SEQ ID NO: 10) |

TABLE I-continued

Primers for Wild-type allele

| | |
|---|---|
| Atspo11-1-3 | N646172U (5' AATCGGTGAGTCAGGTTTCAG 3') (SEQ ID NO: 11) <br> N646172L (5' CCATGGATGAAAGCGATTTAG 3') (SEQ ID NO: 12) |
| Atrec8-3 | N836037U (5'CTCATATTCACGGTGCTCCC 3') (SEQ ID NO: 13) <br> N836037L (5'GGGGGAAAAGAGAAAGGTTC 3') (SEQ ID NO: 14) |

TABLE II

Primers for mutant allele

| | |
|---|---|
| osd1-1 | pst15307L <br> Ds5-2a (5'TCCGTTCCGTTTTCGTTTTTTAC3') (SEQ ID NO: 15) |
| osd1-2 | GT21481U <br> Ds3-4 (5'CCGTCCCGCAAGTTAAATATG3') (SEQ ID NO: 16) |
| Atspo11-1-3 | N646172L <br> LbSalk2 (5' GCTTTCTTCCCTTCCTTTCTC 3') (SEQ ID NO: 17) |
| Atrec8-3 | N836137L <br> LB3sail (5'TAGCATCTGAATTTCATAACCAATC TCGATACAC3') (SEQ ID NO: 18) |

Genetic markers used to genotype the osd1-1(No-0)/osd1-2(Ler)×Col-0 F1 population and osd1-1(No-0)/spo11-1(Col-0)/rec8(Col-0) triple mutant×Ler F1 population are listed in Table III. The PCR conditions were 40 cycles of 30 s at 94° C., 30 s at Tm and 30 s at 72° C.

TABLE III

| Marker | Chrom. | Position Pb | Primer 1 (SEQ ID NO:) | Primer 2 (SEQ ID NO:) |
|---|---|---|---|---|
| Msat1-13 | 1 | 25827433 | CAACCACCAGGCTC (19) | GTCAAACCAGTTCAATCA (20) |
| F5i14 | 1 | 24374008 | CTGCCTGAAATTGTCGAAAC (21) | GGCATCACAGTTCTGATTCC (22) |
| Msat2-18 | 2 | 2799644 | TAGTCTCTTTTGGTGCGCATA (23) | AGCCTCTCCAAGCTTAGGTCT (24) |
| Msat2-21 | 2 | 11461020 | ATTTTTAGCCCAATCACGTTT (25) | AGGTCAAGTGAAAGGGTAAGG (26) |
| Msat2-9 | 2 | 18152580 | TAAAAGAGTCCCTCGTAAAG (27) | GTTGTTGTTGTGGCATT (28) |
| CapsK4_10355 | 4 | 10354800 | ACCCATTTGGTGATGCTAAC (29) | GAGCAGTTTCCACTTTGTCC (30) |
| Msat4-18 | 4 | 11966304 | TGTAAATATCGGCTTCTAAG (31) | CTGAAACAAATCGCATTA (32) |
| Nga151 | 5 | 4669932 | GTTTTGGGAAGTTTTGCTGG (33) | CAGTCTAAAAGCGAGAGTATGATG (34) |

These markers were amplified (40 cycles of 30 s at 94° C., 30 s at 58° C. and 30 s at 72° C.) with the indicated primers and observed after migration on 3% agarose gel.

CAPS K4 10355 was observed after Eco47III/HpaII double digestion. The two primer pairs specific for the osd1-1 and osd1-2 insertion borders were used as a marker on chromosome 3.

Cytology and Flow Cytometry:

Final meiotic products were observed as described in AZUMI et al., (Embo J, 21, 3081-95., 2002) and viewed with a conventional light microscope with a 40× dry objective. Chromosomes spreads and observations were carried out using the technique described in MERCIER et al., (Biochimie, 83, 1023-28, 2001). The DNA fluorescence of spermatic pollen nuclei was quantified using open LAB 4.0.4 software. For each nucleus the surrounding background was calculated and subtracted from the global fluorescence of the nucleus. Meiotic spindles were observed according to the protocol described in MERCIER et al., (Genes Dev, 15, 1859-71, 2001) except that the DNA was counter-stained with DAPI. Observations were made using an SP2 Leica confocal microscope. Images were acquired with a 63× water objective in xyz and 3D reconstructions were made using Leica software. Projections are shown. Cells were imaged at excitation 488 nm and 405 nm with AlexaFluor488 and DAPI respectively. *Arabidopsis* genome sizes were measured as described in MARIE & BROWN, (Biol Cell, 78, 41-51, 1993) using tomato *Lycopersicon esculentum* cv "Montfavet" as the standard. (2C=1.99 pg, % GC=40.0%).

Example 1

Production of Diploid Gametes by Osd1 Mutants

As a part of an expression profiling screen for meiotic genes, using the Expression Angler tool (TOUFIGHI et al., Plant J, 43, 153-63, 2005) with the AtGenExpress tissue set (SCHMID et al., Nat Genet, 37, 501-6, 2005), At3g57860 was selected as a good candidate due to its co-regulation with several known meiotic genes. At3g57860 corresponds to the UVI4-Like gene (UVI4-L) which was briefly described in a study of its paralogue, the UVI4 gene (HASE et al., Plant J, 46, 317-26, 2006). Due to its role in meiosis (see below) we renamed the At3g57860 gene OSD1, for omission of second division. The OSD1 and UVI4 proteins are conserved throughout the plant kingdom but do not contain any obvious conserved known functional domains No homologues were identified outside the plant kingdom.

We investigated the role of the OSD1 gene by isolating and characterising two mutants. The osd1-1 (pst15307) and the osd1-2 (GT21481) Ds insertional mutants are in the Nooseen (No-0) and Landsberg (Ler) backgrounds, respectively, and in both cases the insertion is in the second exon of the OSD1 gene.

Figure 2:
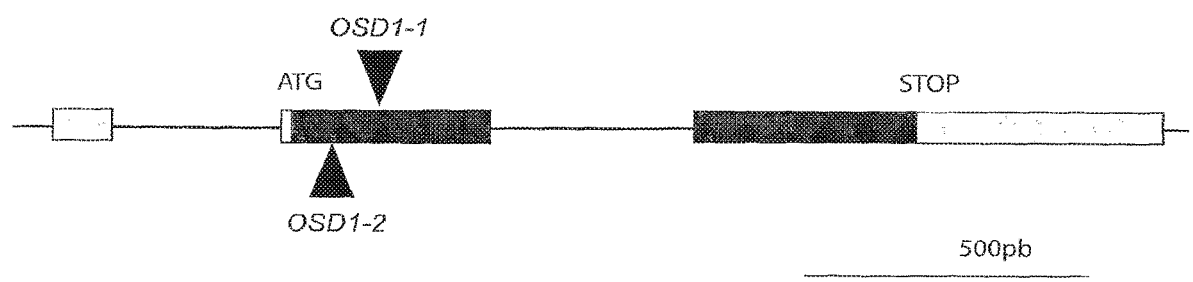
FIG. 2 shows the intron/exon structure of the OSD1 gene and the location of the two different Ds insertions.

The intron/exon structure of the OSD1 gene and the location of the two different Ds insertions are shown in FIG. 2. The OSD1 gene contains 3 exons and 2 introns and encodes a protein of 243 amino acids. The positions of the two Ds insertions are indicated by triangles.

Figure 3:
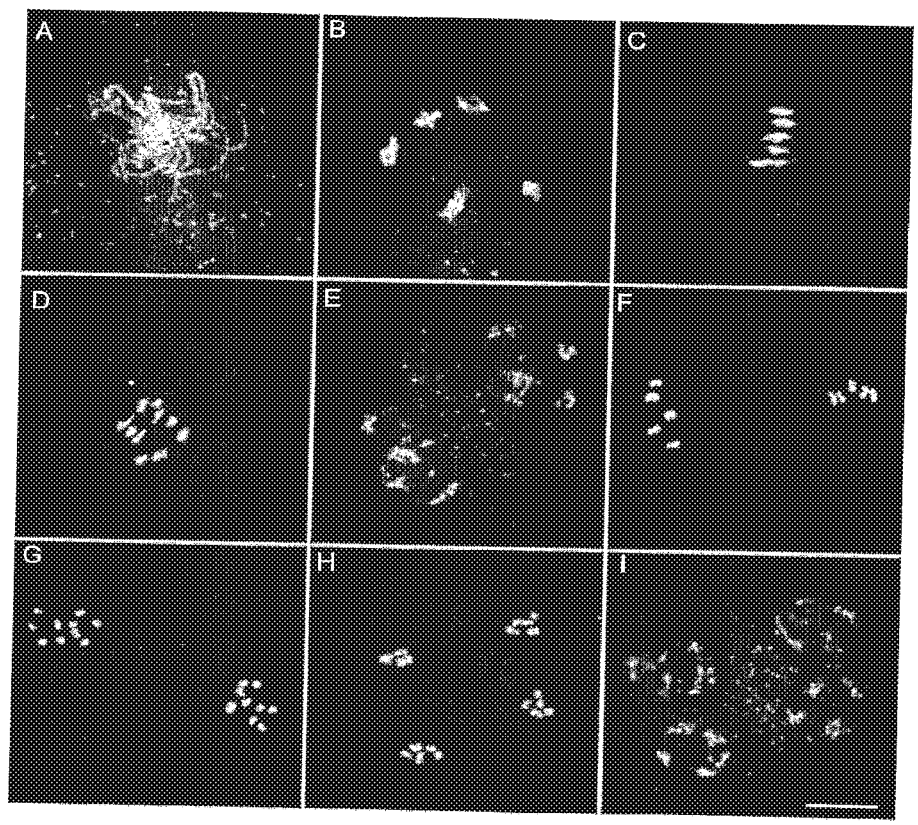
FIG. 3 are images representing meiosis in wild-type plants. Panel A: Pachytene where homologous chromosomes are fully synapsed. Panel B: Diakinesis where five pairs of homologous chromosomes (bivalent), linked by chiasmata, are observed. Panel C: Metaphase I where the five bivalent are aligned on the metaphase plate. Panel D: Anaphase I where the homologous chromosomes are separated. Panel E: Telophase I. Panel F: Metaphase II where pairs of sister chromatids align on the metaphase plates. Panel G: Anaphase II where the sister chromatids are separated. Panels H and I: Telophase I where four haploid spores are formed (tetrad). The scale bar shown is 10 µm.
Figure 4:
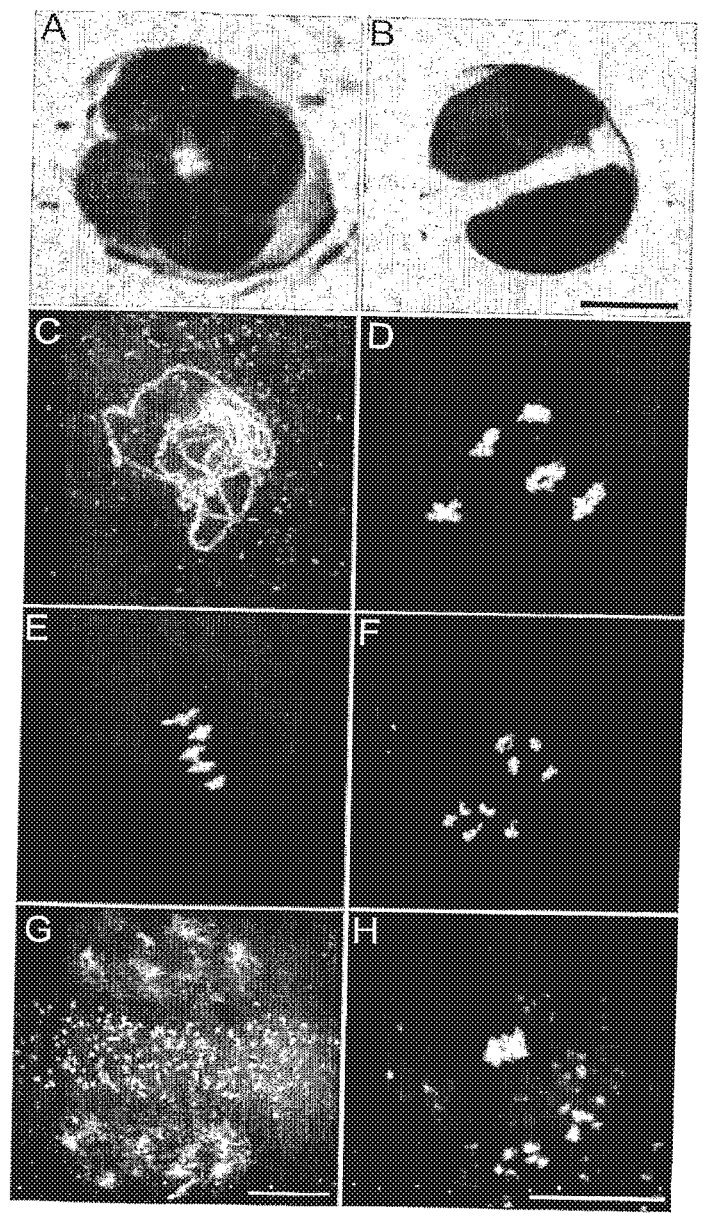
FIG. 4 are images representing meiosis in osd1 mutants. Panels A and B show male meiotic products stained with toluidine blue. Panel A shows a wild type tetrad. Panel B shows a dyad in the osd1-1 mutant. Panels C and D show that male meiosis in osd1 is indistinguishable from wild type until telophase I (compared to FIG. 3, Panel E), but no figures characteristic of a second division were observed. Panel C: Pachytene. Panel D: Diakinesis. Panel E: metaphase I. Panel F: Anaphase I. Panel G: Telophase I. Panel H: Metaphase I of female meiosis in osd1.

FIG. 3 represents meiosis in wild-type plants and FIG. 4 represents meiosis in osd1 mutants.

Legend of FIG. 3: (A) Pachytene. Homologous chromosomes are fully synapsed. (B) Diakinesis. Five pairs of homologous chromosomes (bivalent), linked by chiasmata, are observed. (C) Metaphase I. The five bivalent are aligned on the metaphase plate. (D) Anaphase I. The homologous chromosomes are separated. (E) Telophase I. (F) Metaphase II. The pairs of sister chromatids align on the metaphase plates. (G) Anaphase II. The sister chromatids are separated. (H and I) Telophase II. Four haploid spores are formed (tetrad). Scale bar=10 µm.

Legend of FIG. 4: (A and B) Male meiotic products stained with toluidine blue. (A) A wild type tetrad. (B) A dyad in the osd1-1 mutant. (C to D) Male meiosis in osd1 is indistinguishable from wild type until telophase I (compare to FIG. 3), but no figures characteristic of a second division were observed. (C) pachytene. (D) diakinesis. (E) metaphase I. (F) Anaphase I. (G) Telophase I. (H) Metaphase I of female meiosis in osd1.

In both independent osd1 mutants the products of male meiosis were dyads (osd1-1: 714/714 osd1-2: 334/334) instead of tetrads (FIGS. 4 A and B). Complementation tests between osd1-1 and osd1-2 confirmed that these mutations are allelic (osd1-1/osd1-2: 369 dyads/369), and thus demonstrated that the observed dyads are due to disruption of the OSD1 gene. Osd1 mutants did not show any somatic developmental defects, male and female gametophyte lethality or reduced fertility (wild type 38±11 seeds/fruit, osd1 35±6).

Next, we measured ploidy levels among the offspring of diploid osd1 mutants. Among selfed progeny, tetraploids (84%) and triploids (16%), but no diploid plants were found (osd1-1: n=56; osd1-2: n=24). When mutant pollen was used to fertilise a wild type plant, all the resulting progeny were triploid (osd1-1: n=75). When mutant ovules were fertilised with wild type pollen grains we isolated 12% diploid and 88% triploid plants (n=25). This demonstrated that the osd1 mutants produce high levels of male (100%) and female (85%) diploid spores, which result in functional gametes.

To unravel the mechanisms leading to dyad production in osd1, we investigated chromosome behaviour during meiosis. Both male and female meiosis I were indistinguishable from wild type (compare FIG. 4 with FIG. 3). Notably, chiasmata, the cytological manifestation of crossovers, and bivalents were observed. However, we were unable to find any meiosis II figures (among >500 male meiocytes from prophase to spore formation), strongly suggesting that dyad production is due to an absence of the second meiotic division. If this second division does not take place then any heterozygosis at centromeres will be lost in the diploid gametes because of sister chromatids co-segregation and homologues separation during the first division. Because of recombination, any loci which are not linked to centromeres will segregate. We tested our assumption by taking advantage of the two different genetic backgrounds of the osd1-1 (No-0) and osd1-2 mutants (Ler). F1 plants bearing the two mutations—mutant for osd1 and heterozygous for any No-0/Ler polymorphisms—were crossed as male or female to a third genetic background, Columbia (Col-0). Karyotyping and genotyping of the obtained plants for trimorphic molecular markers provided direct information on the genetic make-up of pollen grains and female gametophytes produced by the mutant. All the diploid gametes tested had the predicted genetic characteristics. They were systematically homozygous at centromeres and segregating—because of recombination—at other loci (n=48 for male diploid gametes and n=41 for female diploid gametes). These results confirmed that the absence of a second meiotic division is indeed the cause of 2n gametes production in osd1. This mechanism also implies that unbalanced chromosome segregation at meiosis I would give rise to unbalanced dyads in osd1; this was confirmed by analysing a double Atspo11-1/osd1-1 mutant (data not shown).

Due to an absence of the second meiotic division, osd1 mutants produce high frequencies of viable diploid male and female gametophytes, which generate, after fecundation, viable tetraploid plants. However, this phenomenon differs from apomeiosis in that the produced gametes are genetically different from the mother plant.

Example 2

Production of Apomeiotic Gametes by Triple Osd1/Atrec8/Atspo11-1 Mutants

In double Atspo11-1/Atrec8 mutants the first meiotic division is replaced by a mitotic-like division, followed by an unbalanced second division which leads to unbalanced spores and sterility (CHELYSHEVA et al., J Cell Sci, 118, 4621-32, 2005).

We generated osd1/Atrec8/Atspo11-1 mutants. Plants heterozygous for both Atspo11-1 and Atrec8 mutations were obtained by crossing plants heterozygous for each mutation, and were crossed by a plant heterozygous for osd1. Triple heterozygous plants identified were self-fertilized and plants homozygous for the three mutations were analyzed.

Figure 5:
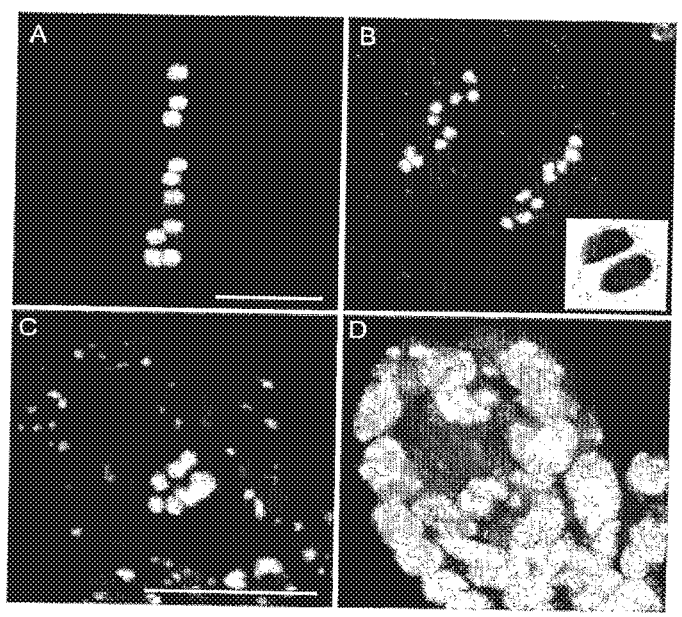
FIG. 5 shows chromosome behaviour during male and female meiosis of osd1/Atrec8/Atspo11-1 mutants. Panel A: Male metaphase I Panel B: Male anaphase I where the vignette (insert) shows a dyad in MiMe. Panel C: Female metaphase I. Panel D: Female anaphase I. The scale bar shown is 10 µm.

Observation of chromosome behaviour during male and female meiosis of these mutants is shown in FIG. 5.

Legend of FIG. 5: (A) Male metaphase I (B) Male anaphase I. The vignette shows a dyad in MiMe. (C) Female metaphase I. (D) Female anaphase I. Scale bar=10 µm.

These observations revealed a mitotic-like division: 10 univalents aligned on the metaphase plate and sister chromatids separated at anaphase (FIG. 5).

The Atspo11-1 and Atrec8 mutations lead to a mitotic-like first meiotic division and the osd1 mutation prevents the second meiotic division from taking place. This results in replacement of meiosis by a mitotic-like division, and in apomeiosis.

We called this genotype MiMe for "mitosis instead of meiosis". MiMe plants generate dyads (408/408) and are fertile (25±6 seeds per fruit). The osd1 mutation therefore suppressed the sterility phenotype of the Atspo11-1/Atrec8 double mutant.

The selfed progeny of MiMe plants were systematically tetraploid (n=24) and backcrosses between diploid MiMe plants and wild type plants generated triploid plants regardless of whether male (n=24) or female (n=67) MiMe gametes were used, showing that this mitotic-like division gives rise to functional diploid gametes. All the gametes (male and female), tested similarly as described above, systematically retained the mother plant heterozygosity for every genetic marker tested and were thus genetically identical to the mother plant. These results confirm that MiMe plants undergo a mitotic-like division instead of a normal meiotic division, without affecting subsequent sexual processes.

When meiosis is replaced by mitosis ploidy is expected to double with each generation. This was observed in MiMe plants, as shown in FIG. 6.

Figure 6:
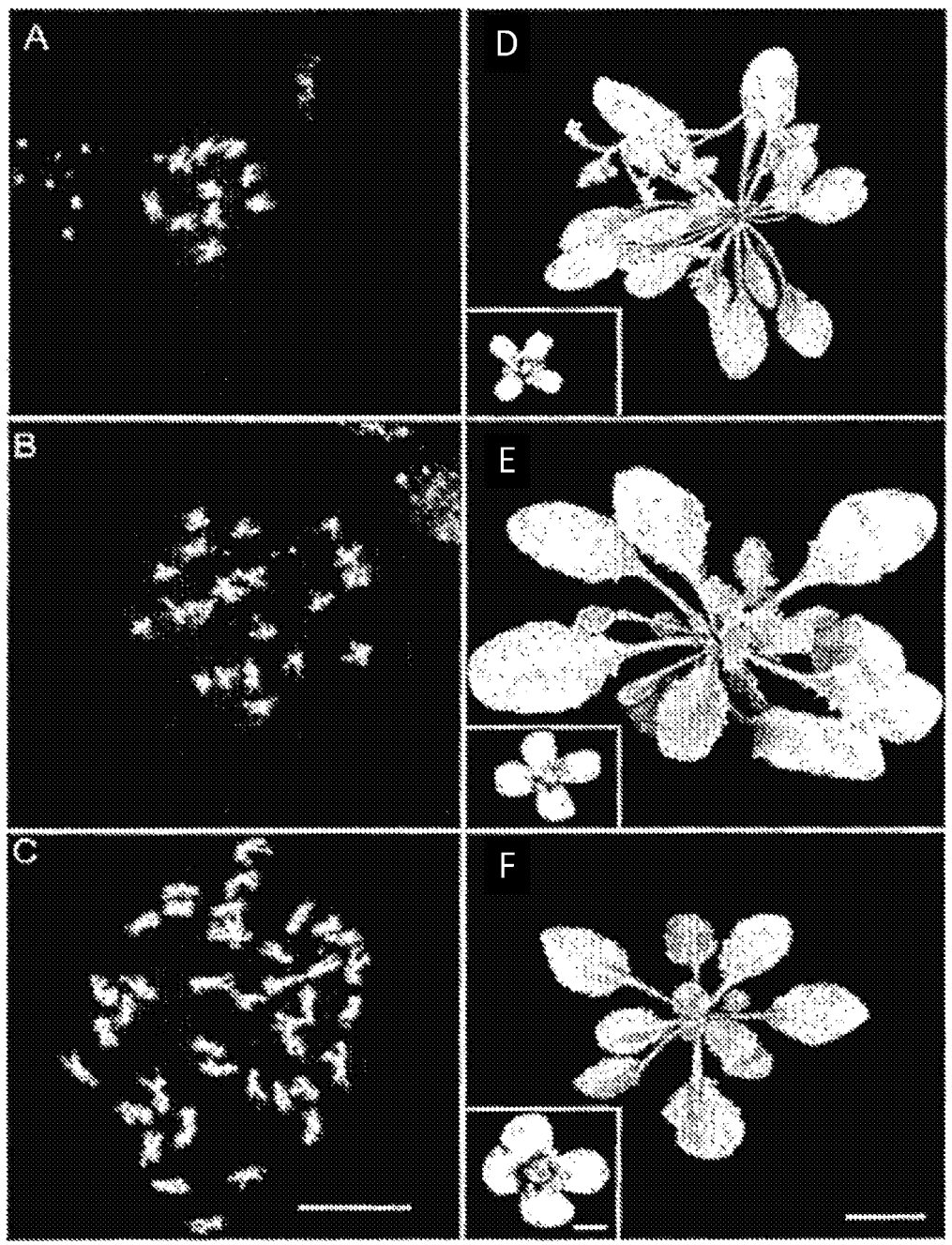
FIG. 6 shows images illustrating that in MiMe plants, when meiosis is replaced by mitosis, ploidy is expected to double with each generation. Left column of images panels A, B and C: show mitotic metaphases, where scale bar=10 µm. Right column of images D, E and F of images, respectively, are the corresponding four weeks old plants (where the scale bar=2 cm) and inserts show flowers (where the scale bar=1 mm).

Legend of FIG. 6: Left column: mitotic metaphase, scale bar=10 µm. Right columns: the corresponding four weeks old plants, (scale bar=2 cm) and flowers (scale bar=1 mm)

In subsequent generations, we obtained tetraploid (4N, 20 chromosomes, n=26) and octoploid (8N, 40 chromosomes, n=33).

Example 3

Identification of a Rice Ortholog of the *Arabidopsis* Osd1 Gene

The *Oriza sativa* genome contains two OSD1/UVI4 homologue candidates (Os02g37850 and Os04g39670). We isolated two T-DNA insertion mutants in one of this putative homologue (Os02g37850). The two lines, AMBA12 and AMQF10 were genotyped by PCR to select homozygotes. In both lines we observed spontaneous tetraploids plants among the offspring of diploid mutant plants, suggestive of the production of functional male and female 2n gametes (AMBA 12: 100% of tetraploid, n=30; AMQF10 37% of tetraploids, n=27). We then studied the meiotic products in AMB12 mutants (n>400) and observed the production of 100% of dyads instead of tetrads, as illustrated by FIG. 7.

Figure 7:
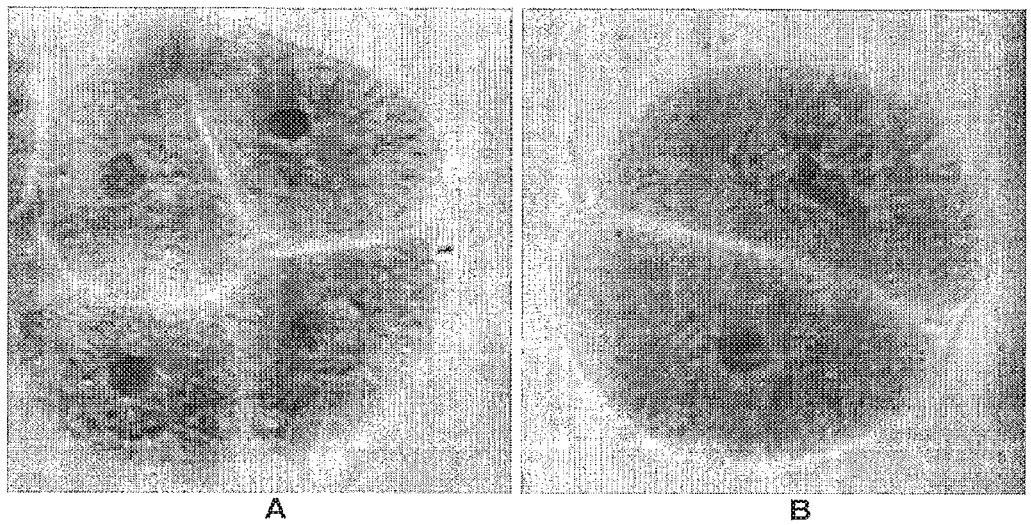
FIG. 7 illustrates the production of 100% of dyads instead of tetrads as meiotic products in AMB12 mutants (n>400). Panel A shows the tetrad of spores in the wild type and Panel B shows the dyad of spores in AMB12.

Legend of FIG. 7: A: Tetrad of spores in wild type; B: Dyad of spores in AMB12.

This phenotype is identical to the *Arabidopsis* osd1 mutant. To unravel the mechanisms leading to dyad production in AMBA12 homozygote mutants, we investigated chromosome behavior during meiosis. Meiosis I was indistinguishable from wild type. Notably, chiasmata, the cytological manifestation of crossovers, and bivalents were observed. However, we were unable to find any meiosis II figures, strongly suggesting that 2N spores production is due to an absence of the second meiotic division, like in *Arabidopsis* osd1. Altogether, these results show that Os02g37850 is the functional homologue of *Arabidopsis* OSD1 and therefore called it OsOSD1. OSD1 and OsOSD1 proteins have 23.6% identity and 35% similarity on an alignment that covers the whole length of the sequences (EMBOSS pairwise alignment Needle tool).

---

We claim:

1. A method for obtaining a plant producing Second Division Restitution 2n gametes, comprising inhibiting in said plant an Omission of Second Division 1 protein (OSD1), wherein said plant is rice, wherein said OSD1 protein has at least 90% sequence identity with the OSD1 protein from *Oryza sativa* (OsOSD1) as set forth in SEQ ID NO: 35, and wherein said protein allows a second meiotic division to occur, and thereby is necessary for the transition from meiosis I to meiosis II, wherein the inhibition of the OSD1 protein is obtained by (i) mutating an OSD1 gene or its promoter and selecting a mutant plant having partially or totally lost OSD1 protein activity, or (ii) expressing a silencing RNA targeting the OSD1 gene encoding said OSD1 protein in said plant, thereby obtaining a rice plant that forms dyads.

2. The method of claim 1, wherein inhibition of the OSD1 protein is obtained by mutating the OSD1 gene or its promoter, and selecting a mutant plant having partially or totally lost the OSD1 protein activity.

3. The method of claim 1, wherein the inhibition of the OSD1 protein is obtained by expressing in said plant a silencing RNA targeting the gene encoding said protein.

4. The method of claim 3, wherein expressing in said plant a silencing RNA comprises expression of a hairpin construct from an expression cassette comprising:

a promoter functional in a plant cell;

at least one DNA construct selected among:

(a) one or more DNA construct(s) of 200 to 1000 bp, each comprising a fragment of a cDNA of OSD1 or its complement, or having at least 95% identity with said fragment, said DNA sequence(s) being placed under transcriptional control of said promoter, (b) one or more hairpin DNA construct(s) capable, when transcribed, of forming a hairpin RNA targeting an OSD1 gene, or (c) one or more DNA construct(s) capable, when transcribed, of forming an miRNA targeting an OSD1 gene said DNA construct(s) being placed under transcriptional control of said promoter.

5. The method of claim 3, wherein expressing in said plant a silencing RNA comprises expression of a hairpin construct from an expression cassette comprising:

a promoter functional in plant cell; and at least one hairpin DNA construct(s) capable, when transcribed, of forming a hairpin RNA targeting an OSD1 gene, said DNA construct(s) being placed under transcriptional control of said promoter.

6. The method of claim 1, wherein inhibition of the OSD1 protein is obtained by mutagenesis of the OSD1 gene or its promoter to provide a plant mutant heterozygous for the mutation and self-fertilizing the mutant plant to obtain a mutant plant homozygous for the mutation.

7. A method for obtaining a plant producing apomeiotic gametes, wherein said plant is rice, wherein said method comprises an inhibition in said plant of the following native plant proteins:

(a) an Omission of Second Division 1 protein (OSD1) havinq at least 90% sequence identity with the OSD1 protein from *Oryza sativa* (OsOSD1) as set forth in SEQ ID NO: 35; and (b) a plant protein involved in initiation of meiotic recombination in plants, said protein being selected among:

(i) a plant sporulation 11-1 (SPO11-1) protein, wherein said protein has at least 40% sequence identity with the SPO11-1 protein of SEQ ID NO: 2;

(ii) a plant sporulation 11-2 (SPO11-2) protein, wherein said protein has at least 40% sequence identity with the SPO11-2 protein of SEQ ID NO: 3;

(iii) a plant putative recombination initiation defect 1 (PRD1) protein, wherein said protein has at least 25% sequence identity with the PRD1 protein of SEQ ID NO: 4; or (iv) a plant homologous pairing aberration in rice 1 (PAIR1) protein, wherein said protein has at least 30% sequence identity with the PAIR1 protein of SEQ ID NO: 5; and (c) a plant meiotic recombination protein 8 (Rec8) protein, wherein said protein has at least 40% sequence identity with the Rec8 protein of SEQ ID NO: 6, wherein the inhibition of at least one of the OSD1, SPO11-1, SPO11-2, PRD1, PAIR1, or Rec8 proteins is obtained by (i) mutating a gene encoding said protein or its promoter and selecting a mutant plant having partially or totally lost an activity of said protein, or (ii) expressing in said plant a silencing RNA targeting the gene encoding said protein.

8. The method of claim 7, wherein inhibition of at least one of the OSD1, SPO11-1, SPO11-2, PRD1, PAIR1, or Rec8 proteins is obtained by mutating a gene encoding said protein or its promoter, and selecting mutants having partially or totally lost the activity of said protein.

9. The method of claim 7, wherein inhibition of at least one of the OSD1, SPO11-1, SPO11-2, PRD1, PAIR1, or Rec8 proteins is obtained by expressing a silencing RNA targeting the gene encoding said protein in said plant.

10. The method of claim 7, comprising the steps of:

(a) providing a plant having a mutation within an allele of the OSD1 gene resulting in the inhibition of the protein encoded by this allele, said plant being heterozygous for this mutation;

(b) providing a plant having a mutation within an allele of a gene selected from the SP011-1, SP011-2, PRD1, PAIR1 gene resulting in the inhibition of the protein encoded by said allele, said plant being heterozygous for this mutation;

(c) providing a plant having a mutation within an allele of the REC8 gene resulting in the inhibition of the protein encoded by said allele, said plant being heterozygous for this mutation; and (d) crossing the plants of steps a) b) and c) in order to obtain a plant having a mutation within an allele of the OSD1 gene, a mutation within an allele of a gene selected from the SP011-1, SP011-2, PRD1, PAIR1 gene, and a mutation within an allele of the REC8 gene, said plant being heterozygous for each mutation; and (e) self-fertilizing the plant of step d) in order to obtain a plant homozygous for the mutation within the OSD1 gene, for the mutation within an allele of a gene selected from the SP011-1, SP011-2, PRD1, PAIR1 gene, and for the mutation within an allele of the REC8 gene.

11. A method for producing Second Division Restitution 2n gametes, wherein said method comprises cultivating a plant obtained by the method of claim 1, and recovering the gametes produced by said plant.

12. A method for producing apomeiotic gametes, wherein said method comprises cultivating a plant obtained by the method of claim 7, and recovering the gametes produced by said plant.

13. A method for obtaining a plant producing Second Division Restitution 2n gametes, comprising inhibiting in said plant an Omission of Second Division 1 protein (OSD1), wherein said plant is rice, wherein said OSD1 protein is the OSD1 protein from *Oryza sativa* (OsOSD1) as set forth in SEQ ID NO: 35, wherein said OSD1 protein allows a second meiotic division to occur, and thereby is necessary for the transition from meiosis I to meiosis II, and wherein the inhibition of said OsOSD1 protein is obtained by (i) mutating an OsOSD1 gene or its promoter and selecting a mutant plant having partially or totally lost OsOSD1 protein activity, or (ii) expressing a silencing RNA targeting the OsOSD1 gene encoding said OsOSD1 protein in said plant, thereby obtaining a rice plant that forms dyads.

* * * * *

SEQUENCE LISTING

<160> NUMBER OF SEQ ID NOS: 35

<210> SEQ ID NO 1
<211> LENGTH: 243
<212> TYPE: PRT
<213> ORGANISM: Arabidopsis thaliana

<400> SEQUENCE: 1

```
Met Pro Glu Ala Arg Asp Arg Thr Glu Arg Pro Val Asp Tyr Ser Thr
1               5                   10                  15

Ile Phe Ala Asn Arg Arg Arg His Gly Ile Leu Leu Asp Glu Pro Asp
            20                  25                  30

Ser Arg Leu Ser Leu Ile Glu Ser Pro Val Asn Pro Asp Ile Gly Ser
        35                  40                  45

Ile Gly Gly Thr Gly Gly Leu Val Arg Gly Asn Phe Thr Thr Trp Arg
    50                  55                  60

Pro Gly Asn Gly Arg Gly Gly His Thr Pro Phe Arg Leu Pro Gln Gly
65                  70                  75                  80

Arg Glu Asn Met Pro Ile Val Thr Ala Arg Gly Arg Gly Gly Gly
                85                  90                  95

Leu Leu Pro Ser Trp Tyr Pro Arg Thr Pro Leu Arg Asp Ile Thr His
            100                 105                 110

Ile Val Arg Ala Ile Glu Arg Arg Arg Gly Ala Gly Thr Gly Gly Asp
        115                 120                 125

Asp Gly Arg Val Ile Glu Ile Pro Thr His Arg Gln Val Gly Val Leu
    130                 135                 140

Glu Ser Pro Val Pro Leu Ser Gly Glu His Lys Cys Ser Met Val Thr
145                 150                 155                 160

Pro Gly Pro Ser Val Gly Phe Lys Arg Ser Cys Pro Pro Ser Thr Ala
                165                 170                 175

Lys Val Gln Lys Met Leu Leu Asp Ile Thr Lys Glu Ile Ala Glu Glu
            180                 185                 190

Glu Ala Gly Phe Ile Thr Pro Glu Lys Lys Leu Leu Asn Ser Ile Asp
        195                 200                 205

Lys Val Glu Lys Ile Val Met Ala Glu Ile Gln Lys Leu Lys Ser Thr
    210                 215                 220

Pro Gln Ala Lys Arg Glu Glu Arg Glu Lys Arg Val Arg Thr Leu Met
225                 230                 235                 240
```

Thr Met Arg

<210> SEQ ID NO 2
<211> LENGTH: 362
<212> TYPE: PRT
<213> ORGANISM: Arabidopsis thaliana

<400> SEQUENCE: 2

```
Met Glu Gly Lys Phe Ala Ile Ser Glu Ser Thr Asn Leu Leu Gln Arg
1               5                   10                  15

Ile Lys Asp Phe Thr Gln Ser Val Val Asp Leu Ala Glu Gly Arg
            20                  25                  30

Ser Pro Lys Ile Ser Ile Asn Gln Phe Arg Asn Tyr Cys Met Asn Pro
            35                  40                  45

Glu Ala Asp Cys Leu Cys Ser Ser Asp Lys Pro Lys Gly Gln Glu Ile
50                  55                  60

Phe Thr Leu Lys Lys Glu Pro Gln Thr Tyr Arg Ile Asp Met Leu Leu
65                  70                  75                  80

Arg Val Leu Leu Ile Val Gln Gln Leu Leu Gln Glu Asn Arg His Ala
                85                  90                  95

Ser Lys Arg Asp Ile Tyr Tyr Met His Pro Ser Ala Phe Lys Ala Gln
            100                 105                 110

Ser Ile Val Asp Arg Ala Ile Gly Asp Ile Cys Ile Leu Phe Gln Cys
            115                 120                 125

Ser Arg Tyr Asn Leu Asn Val Val Ser Val Gly Asn Gly Leu Val Met
130                 135                 140

Gly Trp Leu Lys Phe Arg Glu Ala Gly Arg Lys Phe Asp Cys Leu Asn
145                 150                 155                 160

Ser Leu Asn Thr Ala Tyr Pro Val Pro Val Leu Val Glu Glu Val Glu
                165                 170                 175

Asp Ile Val Ser Leu Ala Glu Tyr Ile Leu Val Val Glu Lys Glu Thr
            180                 185                 190

Val Phe Gln Arg Leu Ala Asn Asp Met Phe Cys Lys Thr Asn Arg Cys
            195                 200                 205

Ile Val Ile Thr Gly Arg Gly Tyr Pro Asp Val Ser Thr Arg Arg Phe
210                 215                 220

Leu Arg Leu Leu Met Glu Lys Leu His Leu Pro Val His Cys Leu Val
225                 230                 235                 240

Asp Cys Asp Pro Tyr Gly Phe Glu Ile Leu Ala Thr Tyr Arg Phe Gly
                245                 250                 255

Ser Met Gln Met Ala Tyr Asp Ile Glu Ser Leu Arg Ala Pro Asp Met
            260                 265                 270

Lys Trp Leu Gly Ala Phe Pro Ser Asp Ser Glu Val Tyr Ser Val Pro
            275                 280                 285

Lys Gln Cys Leu Leu Pro Leu Thr Glu Glu Asp Lys Lys Arg Thr Glu
            290                 295                 300

Ala Met Leu Leu Arg Cys Tyr Leu Lys Arg Glu Met Pro Gln Trp Arg
305                 310                 315                 320

Leu Glu Leu Glu Thr Met Leu Lys Arg Gly Val Lys Phe Glu Ile Glu
                325                 330                 335

Ala Leu Ser Val His Ser Leu Ser Phe Leu Ser Glu Val Tyr Ile Pro
            340                 345                 350

Ser Lys Ile Arg Arg Glu Val Ser Ser Pro
            355                 360
```

<210> SEQ ID NO 3
<211> LENGTH: 383
<212> TYPE: PRT
<213> ORGANISM: Arabidopsis thaliana

<400> SEQUENCE: 3

Met Glu Glu Ser Ser Gly Leu Ser Ser Met Lys Phe Phe Ser Asp Gln
1               5                   10                  15

His Leu Ser Tyr Ala Asp Ile Leu Leu Pro His Glu Ala Arg Ala Arg
            20                  25                  30

Ile Glu Val Ser Val Leu Asn Leu Leu Arg Ile Leu Asn Ser Pro Asp
        35                  40                  45

Pro Ala Ile Ser Asp Leu Ser Leu Ile Asn Arg Lys Arg Ser Asn Ser
    50                  55                  60

Cys Ile Asn Lys Gly Ile Leu Thr Asp Val Ser Tyr Ile Phe Leu Ser
65                  70                  75                  80

Thr Ser Phe Thr Lys Ser Ser Leu Thr Asn Ala Lys Thr Ala Lys Ala
            85                  90                  95

Phe Val Arg Val Trp Lys Val Met Glu Ile Cys Phe Gln Ile Leu Leu
        100                 105                 110

Gln Glu Lys Arg Val Thr Gln Arg Glu Leu Phe Tyr Lys Leu Leu Cys
    115                 120                 125

Asp Ser Pro Asp Tyr Phe Ser Ser Gln Ile Glu Val Asn Arg Ser Val
130                 135                 140

Gln Asp Val Val Ala Leu Leu Arg Cys Ser Arg Tyr Ser Leu Gly Ile
145                 150                 155                 160

Met Ala Ser Ser Arg Gly Leu Val Ala Gly Arg Leu Phe Leu Gln Glu
            165                 170                 175

Pro Gly Lys Glu Ala Val Asp Cys Ser Ala Cys Gly Ser Ser Gly Phe
        180                 185                 190

Ala Ile Thr Gly Asp Leu Asn Leu Leu Asp Asn Thr Ile Met Arg Thr
    195                 200                 205

Asp Ala Arg Tyr Ile Ile Ile Val Glu Lys His Ala Ile Phe His Arg
210                 215                 220

Leu Val Glu Asp Arg Val Phe Asn His Ile Pro Cys Val Phe Ile Thr
225                 230                 235                 240

Ala Lys Gly Tyr Pro Asp Ile Ala Thr Arg Phe Leu His Arg Met
            245                 250                 255

Ser Thr Thr Phe Pro Asp Leu Pro Ile Leu Val Leu Asp Trp Asn
        260                 265                 270

Pro Ala Gly Leu Ala Ile Leu Cys Thr Phe Lys Phe Gly Ser Ile Gly
    275                 280                 285

Met Gly Leu Glu Ala Tyr Arg Tyr Ala Cys Asn Val Lys Trp Ile Gly
290                 295                 300

Leu Arg Gly Asp Asp Leu Asn Leu Ile Pro Glu Glu Ser Leu Val Pro
305                 310                 315                 320

Leu Lys Pro Lys Asp Ser Gln Ile Ala Lys Ser Leu Leu Ser Ser Lys
            325                 330                 335

Ile Leu Gln Glu Asn Tyr Ile Glu Glu Leu Ser Leu Met Val Gln Thr
        340                 345                 350

Gly Lys Arg Ala Glu Ile Glu Ala Leu Tyr Cys His Gly Tyr Asn Tyr
    355                 360                 365

Leu Gly Lys Tyr Ile Ala Thr Lys Ile Val Gln Gly Lys Tyr Ile

<210> SEQ ID NO 4
<211> LENGTH: 1330
<212> TYPE: PRT
<213> ORGANISM: Arabidopsis thaliana

<400> SEQUENCE: 4

```
Met Phe Phe Gln His Ser Gln Leu Gln Asn Ser Asp His Leu Leu His
 1               5                  10                  15

Glu Ser Met Ala Asp Ser Asn His Gln Ser Leu Ser Pro Pro Cys Ala
                20                  25                  30

Asn Gly His Arg Ser Thr Ile Ser Leu Arg Asp Asp Gln Gly Gly Thr
            35                  40                  45

Phe Cys Leu Ile Cys Phe Ser Asn Leu Val Ser Asp Pro Arg Ile Pro
        50                  55                  60

Thr Val His Val Ser Tyr Ala Leu His Gln Leu Ser Ile Ala Ile Ser
 65                  70                  75                  80

Glu Pro Ile Phe Leu Arg Thr Leu Leu Ser His Ile His Phe Leu
                85                  90                  95

Val Ser Pro Leu Val His Ala Leu Ser Ser Ile Asp Asp Ala Pro Ile
            100                 105                 110

Ala Ile Gln Ile Met Asp Met Ile Ser Leu Leu Cys Ser Val Glu Glu
        115                 120                 125

Ser Ser Ile Gly Glu Asp Phe Val Glu Arg Ile Ser Asp Gln Leu Ser
130                 135                 140

Ser Gly Ala Leu Gly Trp Ser Arg Arg Gln Leu His Met Leu His Cys
145                 150                 155                 160

Phe Gly Val Leu Met Ser Cys Glu Asn Ile Asp Ile Asn Ser His Ile
                165                 170                 175

Arg Asp Lys Glu Ala Leu Val Cys Gln Leu Val Glu Gly Leu Gln Leu
            180                 185                 190

Pro Ser Glu Glu Ile Arg Gly Glu Ile Leu Phe Ala Leu Tyr Lys Phe
        195                 200                 205

Ser Ala Leu Gln Phe Thr Glu Gln Asn Val Asp Gly Ile Glu Val Leu
    210                 215                 220

Ser Leu Leu Cys Pro Lys Leu Leu Cys Leu Ser Leu Glu Ala Leu Ala
225                 230                 235                 240

Lys Thr Gln Arg Asp Asp Val Arg Leu Asn Cys Val Ala Leu Leu Thr
                245                 250                 255

Ile Leu Ala Gln Gln Gly Leu Leu Ala Asn Ser His Ser Asn Ser Ala
            260                 265                 270

Ser Ser Met Ser Leu Asp Glu Val Asp Asp Pro Met Gln Thr Ala
        275                 280                 285

Glu Asn Val Ala Ala Arg Pro Cys Leu Asn Val Leu Phe Ala Glu Ala
    290                 295                 300

Ile Lys Gly Pro Leu Leu Ser Thr Asp Ser Glu Val Gln Ile Lys Thr
305                 310                 315                 320

Leu Asp Leu Ile Phe His Tyr Ile Ser Gln Glu Ser Thr Pro Ser Lys
                325                 330                 335

Gln Ile Gln Val Met Val Glu Glu Asn Val Ala Asp Tyr Ile Phe Glu
            340                 345                 350

Ile Leu Arg Leu Ser Glu Cys Lys Asp Gln Val Val Asn Ser Cys Leu
        355                 360                 365
```

-continued

Arg Val Leu Asp Leu Phe Ser Leu Ala Glu His Ser Phe Arg Lys Arg
    370                 375                 380

Leu Val Ile Gly Phe Pro Ser Val Ile Arg Val Leu His Tyr Val Gly
385                 390                 395                 400

Glu Val Pro Cys His Pro Phe Gln Ile Gln Thr Leu Lys Leu Ile Ser
                    405                 410                 415

Ser Cys Ile Ser Asp Phe Pro Gly Ile Ala Ser Ser Ser Gln Val Gln
            420                 425                 430

Glu Ile Ala Leu Val Leu Lys Lys Met Leu Glu Arg Tyr Tyr Ser Gln
        435                 440                 445

Glu Met Gly Leu Phe Pro Asp Ala Phe Ala Ile Ile Cys Ser Val Phe
    450                 455                 460

Val Ser Leu Met Lys Thr Pro Ser Phe Gly Glu Thr Ala Asp Val Leu
465                 470                 475                 480

Thr Ser Leu Gln Glu Ser Leu Arg His Ser Ile Leu Ala Ser Leu Ser
                485                 490                 495

Leu Pro Glu Lys Asp Ser Thr Gln Ile Leu His Ala Val Tyr Leu Leu
            500                 505                 510

Asn Glu Ile Tyr Val Tyr Cys Thr Ala Ser Thr Ser Ile Asn Met Thr
        515                 520                 525

Ser Cys Ile Glu Leu Arg His Cys Val Ile Asp Val Cys Thr Ser His
    530                 535                 540

Leu Leu Pro Trp Phe Leu Ser Asp Val Asn Glu Val Asn Glu Glu Ala
545                 550                 555                 560

Thr Leu Gly Ile Met Glu Thr Phe His Ser Ile Leu Leu Gln Asn Ser
                565                 570                 575

Asp Ile Gln Ala Lys Glu Phe Ala Glu Leu Leu Val Ser Ala Asp Trp
            580                 585                 590

Phe Ser Phe Ser Phe Gly Cys Leu Gly Asn Phe Cys Thr Asp Asn Met
        595                 600                 605

Lys Gln Arg Ile Tyr Leu Met Leu Ser Ser Leu Val Asp Ile Leu Leu
    610                 615                 620

Glu Gln Lys Thr Gly Ser His Ile Arg Asp Ala Leu His Cys Leu Pro
625                 630                 635                 640

Ser Asp Pro Gln Asp Leu Leu Phe Leu Leu Gly Gln Ala Ser Ser Asn
                645                 650                 655

Asn Gln Glu Leu Ala Ser Cys Gln Ser Ala Ala Leu Leu Ile Phe His
            660                 665                 670

Thr Ser Ser Ile Tyr Asn Asp Arg Leu Ala Asp Lys Leu Val Leu
        675                 680                 685

Ala Ser Leu Glu Gln Tyr Ile Ile Leu Asn Lys Thr Ser Leu Ile Cys
    690                 695                 700

Ala Ile Ser Asp Ser Pro Ala Leu Leu Asn Leu Val Asn Leu Tyr Gly
705                 710                 715                 720

Leu Cys Arg Ser Leu Gln Asn Glu Arg Tyr Gln Ile Ser Tyr Ser Leu
                725                 730                 735

Glu Ala Glu Arg Ile Ile Phe His Leu Leu Asn Glu Tyr Glu Trp Asp
            740                 745                 750

Leu Gly Ser Ile Asn Ile His Leu Glu Ser Leu Lys Trp Leu Phe Gln
        755                 760                 765

Gln Glu Ser Ile Ser Lys Ser Leu Ile Tyr Gln Ile Gln Lys Ile Ser
    770                 775                 780

Arg Asn Asn Leu Ile Gly Asn Glu Val His Asn Val Tyr Gly Asp Gly

```
            785                 790                 795                 800
        Arg Gln Arg Ser Leu Thr Tyr Trp Phe Ala Lys Leu Ile Ser Glu Gly
                        805                 810                 815
        Asp Asn Tyr Ala Ala Thr Leu Leu Val Asn Leu Leu Thr Gln Leu Ala
                        820                 825                 830
        Glu Lys Glu Glu Gln Glu Asn Asp Val Thr Ser Ile Leu Asn Leu Met
                        835                 840                 845
        Asn Thr Ile Val Ser Ile Phe Pro Thr Ala Ser Asn Asn Leu Ser Met
                        850                 855                 860
        Asn Gly Ile Gly Ser Val Val His Arg Leu Val Ser Gly Phe Ser Asn
        865                 870                 875                 880
        Ser Ser Leu Gly Thr Ser Phe Lys Thr Leu Leu Leu Val Phe Asn
                        885                 890                 895
        Ile Leu Thr Ser Val Gln Pro Ala Val Leu Met Ile Asp Glu Ser Trp
                        900                 905                 910
        Tyr Ala Val Ser Ile Lys Leu Leu Asn Phe Leu Ser Leu Arg Asp Thr
                        915                 920                 925
        Ala Ile Lys Gln Asn His Glu Asp Met Val Val Ile Gly Ile Leu Ser
                        930                 935                 940
        Leu Val Leu Tyr His Ser Ser Asp Gly Ala Leu Val Glu Ala Ser Arg
        945                 950                 955                 960
        Asn Ile Val Ser Asn Ser Tyr Leu Val Ser Ala Ile Asn Thr Val Val
                        965                 970                 975
        Asp Val Ala Cys Ser Lys Gly Pro Ala Leu Thr Gln Cys Gln Asp Glu
                        980                 985                 990
        Thr Asn Ile Gly Glu Ala Leu Ala Phe Thr Leu Leu Leu Tyr Phe Phe
                        995                 1000                1005
        Ser Leu Arg Ser Leu Gln Ile Val Leu Ala Gly Ala Val Asp Trp
                        1010                1015                1020
        Gln Ala Phe Phe Gly Thr Ser Thr Ser Leu Glu Thr Leu Pro Val
                        1025                1030                1035
        Val Cys Ile Tyr Cys His Asn Leu Cys Arg Leu Met His Phe Gly
                        1040                1045                1050
        Ala Pro Gln Ile Lys Leu Ile Ala Ser Tyr Cys Leu Leu Glu Leu
                        1055                1060                1065
        Leu Thr Gly Leu Ser Glu Gln Val Asp Ile Lys Lys Glu Gln Leu
                        1070                1075                1080
        Gln Cys Ser Ser Ser Tyr Leu Lys Ser Met Lys Ala Val Leu Gly
                        1085                1090                1095
        Gly Leu Val Phe Cys Asp Asp Ile Arg Val Ala Thr Asn Ser Ala
                        1100                1105                1110
        Leu Cys Leu Ser Met Ile Leu Gly Trp Glu Asp Met Glu Gly Arg
                        1115                1120                1125
        Thr Glu Met Leu Lys Thr Ser Ser Trp Tyr Arg Phe Ile Ala Glu
                        1130                1135                1140
        Glu Met Ser Val Ser Leu Ala Leu Pro Cys Ser Ala Ser Ser Thr
                        1145                1150                1155
        Tyr Val Asn His His Lys Pro Ala Val Tyr Leu Thr Val Ala Met
                        1160                1165                1170
        Leu Arg Leu Lys Asn Lys Pro Val Trp Leu Arg Thr Val Phe Asp
                        1175                1180                1185
        Glu Ser Cys Ile Ser Ser Met Ile Gln Asn Leu Asn Gly Ile Asn
                        1190                1195                1200
```

```
Ile Ser Arg Glu Ile Val Ile Leu Phe Arg Glu Leu Met Gln Ala
    1205                1210                1215

Glu Leu Leu Asn Ser Gln Gln Val Thr Lys Leu Asp Arg Ala Phe
    1220                1225                1230

Gln Glu Cys Arg Lys Gln Met His Arg Asn Gly Thr Arg Asp Glu
    1235                1240                1245

Thr Val Glu Glu Gln Val Gln Arg Lys Ile Pro Ser Ile His Asp
    1250                1255                1260

His Ser Glu Phe Cys Asn Tyr Leu Val His Leu Met Val Ser Asn
    1265                1270                1275

Ser Phe Gly His Pro Ser Glu Ser Glu Thr Tyr Thr Gln Lys Lys
    1280                1285                1290

Lys Gln Ile Leu Asp Glu Met Glu Gln Leu Ser Glu Leu Ile Ser
    1295                1300                1305

Thr Arg Glu Gly Arg Val Ser Pro Ile Gln Glu Glu Thr Arg Gln
    1310                1315                1320

Met Gln Thr Glu Arg Ile Val
    1325                1330

<210> SEQ ID NO 5
<211> LENGTH: 449
<212> TYPE: PRT
<213> ORGANISM: Arabidopsis thaliana

<400> SEQUENCE: 5

Met Lys Met Asn Ile Asn Lys Ala Cys Asp Leu Lys Ser Ile Ser Val
1               5                   10                  15

Phe Pro Pro Asn Leu Arg Arg Ser Ala Glu Pro Gln Ala Ser Gln Gln
                20                  25                  30

Leu Arg Ser Gln Gln Ser Gln Gln Ser Phe Ser Gln Gly Pro Ser Ser
            35                  40                  45

Ser Gln Arg Gly Cys Gly Gly Phe Ser Gln Met Thr Gln Ser Ser Ile
        50                  55                  60

Asp Glu Leu Leu Ile Asn Asp Gln Arg Phe Ser Ser Gln Glu Arg Asp
65                  70                  75                  80

Leu Ser Leu Lys Lys Val Ser Ser Cys Leu Pro Pro Ile Asn His Lys
                85                  90                  95

Arg Glu Asp Ser Gln Leu Val Ala Ser Arg Ser Ser Ser Gly Leu Ser
                100                 105                 110

Arg Arg Trp Ser Ser Ala Ser Ile Gly Glu Ser Lys Ser Gln Ile Ser
            115                 120                 125

Glu Glu Leu Glu Gln Arg Phe Gly Met Met Glu Thr Ser Leu Ser Arg
        130                 135                 140

Phe Gly Met Met Leu Asp Ser Ile Gln Ser Asp Ile Met Gln Ala Asn
145                 150                 155                 160

Arg Gly Thr Lys Glu Val Phe Leu Glu Thr Glu Arg Ile Gln Gln Lys
                165                 170                 175

Leu Thr Leu Gln Asp Thr Ser Leu Gln Gln Leu Arg Lys Glu Gln Ala
                180                 185                 190

Asp Ser Lys Ala Ser Leu Asp Gly Gly Val Lys Phe Ile Leu Glu Glu
            195                 200                 205

Phe Ser Lys Asp Pro Asn Gln Glu Lys Leu Gln Lys Ile Leu Gln Met
        210                 215                 220

Leu Thr Thr Ile Pro Glu Gln Val Glu Thr Ala Leu Gln Lys Ile Gln
```

```
            225                 230                 235                 240
Arg Glu Ile Cys His Thr Phe Thr Arg Glu Ile Gln Val Leu Ala Ser
                        245                 250                 255

Leu Arg Thr Pro Glu Pro Arg Val Arg Val Pro Thr Ala Pro Gln Val
                260                 265                 270

Lys Ala Lys Glu Asn Leu Pro Glu Gln Arg Gly Gln Ala Ala Lys Val
            275                 280                 285

Leu Thr Ser Leu Lys Met Pro Glu Pro Arg Val Gln Val Pro Ala Ala
        290                 295                 300

Pro Gln Ala Lys Glu Asn Phe Pro Glu Gln Arg Gly Pro Val Ala Lys
305                 310                 315                 320

Ser Asn Ser Phe Cys Asn Thr Thr Leu Lys Thr Lys Gln Pro Gln Phe
                    325                 330                 335

Pro Arg Asn Pro Asn Asp Ala Ser Ala Arg Ala Val Lys Pro Tyr Leu
                340                 345                 350

Ser Pro Lys Ile Gln Val Gly Cys Trp Lys Thr Val Lys Pro Glu Lys
            355                 360                 365

Ser Asn Phe Lys Lys Arg Ala Thr Arg Lys Pro Val Lys Ser Glu Ser
        370                 375                 380

Thr Arg Thr Gln Phe Glu Gln Cys Ser Val Val Ile Asp Ser Asp Glu
385                 390                 395                 400

Glu Asp Ile Asp Gly Gly Phe Ser Cys Leu Ile Asn Glu Asn Thr Arg
                    405                 410                 415

Gly Thr Asn Phe Glu Trp Asp Ala Glu Lys Glu Thr Glu Arg Ile Leu
                420                 425                 430

Arg Thr Ala Arg Arg Thr Lys Arg Lys Phe Gly Asn Pro Ile Ile Ile
            435                 440                 445

Asn

<210> SEQ ID NO 6
<211> LENGTH: 617
<212> TYPE: PRT
<213> ORGANISM: Arabidopsis thaliana

<400> SEQUENCE: 6

Met Phe Tyr Ser His Gln Leu Leu Ala Arg Lys Ala Pro Leu Gly Gln
1               5                   10                  15

Ile Trp Met Ala Ala Thr Leu His Ala Lys Ile Asn Arg Lys Lys Leu
            20                  25                  30

Asp Lys Leu Asp Ile Ile Gln Ile Cys Glu Glu Ile Leu Asn Pro Ser
        35                  40                  45

Val Pro Met Ala Leu Arg Leu Ser Gly Ile Leu Met Gly Gly Val Val
    50                  55                  60

Ile Val Tyr Glu Arg Lys Val Lys Leu Leu Phe Asp Asp Val Asn Arg
65                  70                  75                  80

Phe Leu Val Glu Ile Asn Gly Ala Trp Arg Thr Lys Ser Val Pro Asp
                85                  90                  95

Pro Thr Leu Leu Pro Lys Gly Lys Thr His Ala Arg Lys Glu Ala Val
            100                 105                 110

Thr Leu Pro Glu Asn Glu Ala Asp Phe Gly Asp Phe Glu Gln Thr
        115                 120                 125

Arg Asn Val Pro Lys Phe Gly Asn Tyr Met Asp Phe Gln Gln Thr Phe
    130                 135                 140

Ile Ser Met Arg Leu Asp Glu Ser His Val Asn Asn Asn Pro Glu Pro
```

```
            145                 150                 155                 160
Glu Asp Leu Gly Gln Gln Phe His Gln Ala Asp Ala Glu Asn Ile Thr
                165                 170                 175

Leu Phe Glu Tyr His Gly Ser Phe Gln Thr Asn Asn Glu Thr Tyr Asp
                180                 185                 190

Arg Phe Glu Arg Phe Asp Ile Glu Gly Asp Asp Glu Thr Gln Met Asn
                195                 200                 205

Ser Asn Pro Arg Glu Gly Ala Glu Ile Pro Thr Thr Leu Ile Pro Ser
        210                 215                 220

Pro Pro Arg His His Asp Ile Pro Glu Gly Val Asn Pro Thr Ser Pro
225                 230                 235                 240

Gln Arg Gln Glu Gln Glu Asn Arg Arg Asp Gly Phe Ala Glu Gln
                245                 250                 255

Met Glu Glu Gln Asn Ile Pro Asp Lys Glu His Asp Arg Pro Gln
                260                 265                 270

Pro Ala Lys Lys Arg Ala Arg Lys Thr Ala Thr Ser Ala Met Asp Tyr
                275                 280                 285

Glu Gln Thr Ile Ile Ala Gly His Val Tyr Gln Ser Trp Leu Gln Asp
        290                 295                 300

Thr Ser Asp Ile Leu Cys Arg Gly Glu Lys Arg Val Arg Gly Thr
305                 310                 315                 320

Ile Arg Pro Asp Met Glu Ser Phe Lys Arg Ala Asn Met Pro Pro Thr
                325                 330                 335

Gln Leu Phe Glu Lys Asp Ser Ser Tyr Pro Pro Gln Leu Tyr Gln Leu
                340                 345                 350

Trp Ser Lys Asn Thr Gln Val Leu Gln Thr Ser Ser Ser Glu Ser Arg
        355                 360                 365

His Pro Asp Leu Arg Ala Glu Gln Ser Pro Gly Phe Val Gln Glu Arg
        370                 375                 380

Met His Asn His His Gln Thr Asp His His Glu Arg Ser Asp Thr Ser
385                 390                 395                 400

Ser Gln Asn Leu Asp Ser Pro Ala Glu Ile Leu Arg Thr Val Arg Thr
                405                 410                 415

Gly Lys Gly Ala Ser Val Glu Ser Met Met Ala Gly Ser Arg Ala Ser
                420                 425                 430

Pro Glu Thr Ile Asn Arg Gln Ala Ala Asp Ile Asn Val Thr Pro Phe
                435                 440                 445

Tyr Ser Gly Asp Asp Val Arg Ser Met Pro Ser Thr Pro Ser Ala Arg
        450                 455                 460

Gly Ala Ala Ser Ile Asn Asn Ile Glu Ile Ser Ser Lys Ser Arg Met
465                 470                 475                 480

Pro Asn Arg Lys Arg Pro Asn Ser Ser Pro Arg Arg Gly Leu Glu Pro
                485                 490                 495

Val Ala Glu Glu Arg Pro Trp Glu His Arg Glu Tyr Glu Phe Glu Phe
                500                 505                 510

Ser Met Leu Pro Glu Lys Arg Phe Thr Ala Asp Lys Glu Ile Leu Phe
                515                 520                 525

Glu Thr Ala Ser Thr Gln Thr Gln Lys Pro Val Cys Asn Gln Ser Asp
                530                 535                 540

Glu Met Ile Thr Asp Ser Ile Lys Ser His Leu Lys Thr His Phe Glu
545                 550                 555                 560

Thr Pro Gly Ala Pro Gln Val Glu Ser Leu Asn Lys Leu Ala Val Gly
                565                 570                 575
```

```
Met Asp Arg Asn Ala Ala Ala Lys Leu Phe Phe Gln Ser Cys Val Leu
            580                 585                 590

Ala Thr Arg Gly Val Ile Lys Val Asn Gln Ala Glu Pro Tyr Gly Asp
        595                 600                 605

Ile Leu Ile Ala Arg Gly Pro Asn Met
        610                 615
```

```
<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
cgtcactctc cccaagaaag                                               20

<210> SEQ ID NO 8
<211> LENGTH: 20
<212> TYPE: DNA
<213> ORGANISM: Artificial
<220> FEATURE:
<223> OTHER INFORMATION: PCR primer

<400> SEQUENCE: 8
ggctaagcaa gcctgctatg                                               20

<210> SEQ ID NO 9
<211> LENGTH: 19
<212> TYPE: DNA
<213> ORGANISM: Artificial
<220> FEATURE:
<223> OTHER INFORMATION: PCR primer

<400> SEQUENCE: 9
ccggtgttct tgtgactcg                                                19

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
gcagattcct aattcagctc                                               20

<210> SEQ ID NO 11
<211> LENGTH: 21
<212> TYPE: DNA
<213> ORGANISM: Artificial
<220> FEATURE:
<223> OTHER INFORMATION: PCR primer

<400> SEQUENCE: 11
aatcggtgag tcaggtttca g                                             21

<210> SEQ ID NO 12
<211> LENGTH: 21
<212> TYPE: DNA
<213> ORGANISM: Artificial
<220> FEATURE:
<223> OTHER INFORMATION: PCR primer

<400> SEQUENCE: 12
```

```
ccatggatga aagcgattta g                                        21

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
ctcatattca cggtgctccc                                          20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
gggggaaaag agaaaggttc                                          20

<210> SEQ ID NO 15
<211> LENGTH: 23
<212> TYPE: DNA
<213> ORGANISM: Artificial
<220> FEATURE:
<223> OTHER INFORMATION: PCR primer

<400> SEQUENCE: 15
tccgttccgt tttcgttttt tac                                      23

<210> SEQ ID NO 16
<211> LENGTH: 21
<212> TYPE: DNA
<213> ORGANISM: Artificial
<220> FEATURE:
<223> OTHER INFORMATION: PCR primer

<400> SEQUENCE: 16
ccgtcccgca agttaaatat g                                        21

<210> SEQ ID NO 17
<211> LENGTH: 21
<212> TYPE: DNA
<213> ORGANISM: Artificial
<220> FEATURE:
<223> OTHER INFORMATION: PCR primer

<400> SEQUENCE: 17
gctttcttcc cttcctttct c                                        21

<210> SEQ ID NO 18
<211> LENGTH: 34
<212> TYPE: DNA
<213> ORGANISM: Artificial
<220> FEATURE:
<223> OTHER INFORMATION: PCR primer

<400> SEQUENCE: 18
tagcatctga atttcataac caatctcgat acac                          34

<210> SEQ ID NO 19
<211> LENGTH: 14
<212> TYPE: DNA
```

```
<213> ORGANISM: Artificial
<220> FEATURE:
<223> OTHER INFORMATION: PCR primer

<400> SEQUENCE: 19
caaccaccag gctc                                                        14

<210> SEQ ID NO 20
<211> LENGTH: 18
<212> TYPE: DNA
<213> ORGANISM: Artificial
<220> FEATURE:
<223> OTHER INFORMATION: PCR primer

<400> SEQUENCE: 20
gtcaaaccag ttcaatca                                                    18

<210> SEQ ID NO 21
<211> LENGTH: 20
<212> TYPE: DNA
<213> ORGANISM: Artificial
<220> FEATURE:
<223> OTHER INFORMATION: PCR primer

<400> SEQUENCE: 21
ctgcctgaaa ttgtcgaaac                                                  20

<210> SEQ ID NO 22
<211> LENGTH: 20
<212> TYPE: DNA
<213> ORGANISM: Artificial
<220> FEATURE:
<223> OTHER INFORMATION: PCR primer

<400> SEQUENCE: 22
ggcatcacag ttctgattcc                                                  20

<210> SEQ ID NO 23
<211> LENGTH: 21
<212> TYPE: DNA
<213> ORGANISM: Artificial
<220> FEATURE:
<223> OTHER INFORMATION: PCR primer

<400> SEQUENCE: 23
tagtctcttt tggtgcgcat a                                                21

<210> SEQ ID NO 24
<211> LENGTH: 21
<212> TYPE: DNA
<213> ORGANISM: Artificial
<220> FEATURE:
<223> OTHER INFORMATION: PCR primer

<400> SEQUENCE: 24
agcctctcca agcttaggtc t                                                21

<210> SEQ ID NO 25
<211> LENGTH: 21
<212> TYPE: DNA
<213> ORGANISM: Artificial
<220> FEATURE:
<223> OTHER INFORMATION: PCR primer

<400> SEQUENCE: 25 attttagcc caatcacgtt t                                                 21
```

<210> SEQ ID NO 26
<211> LENGTH: 21
<212> TYPE: DNA
<213> ORGANISM: Artificial
<220> FEATURE:
<223> OTHER INFORMATION: PCR primer

<400> SEQUENCE: 26
aggtcaagtg aaagggtaag g                                    21

<210> SEQ ID NO 27
<211> LENGTH: 20
<212> TYPE: DNA
<213> ORGANISM: Artificial
<220> FEATURE:
<223> OTHER INFORMATION: PCR primer

<400> SEQUENCE: 27
taaaagagtc cctcgtaaag                                      20

<210> SEQ ID NO 28
<211> LENGTH: 17
<212> TYPE: DNA
<213> ORGANISM: Artificial
<220> FEATURE:
<223> OTHER INFORMATION: PCR primer

<400> SEQUENCE: 28
gttgttgttg tggcatt                                         17

<210> SEQ ID NO 29
<211> LENGTH: 20
<212> TYPE: DNA
<213> ORGANISM: Artificial
<220> FEATURE:
<223> OTHER INFORMATION: PCR primer

<400> SEQUENCE: 29
acccatttgg tgatgctaac                                      20

<210> SEQ ID NO 30
<211> LENGTH: 20
<212> TYPE: DNA
<213> ORGANISM: Artificial
<220> FEATURE:
<223> OTHER INFORMATION: PCR primer

<400> SEQUENCE: 30
gagcagtttc cactttgtcc                                      20

<210> SEQ ID NO 31
<211> LENGTH: 20
<212> TYPE: DNA
<213> ORGANISM: Artificial
<220> FEATURE:
<223> OTHER INFORMATION: PCR primer

<400> SEQUENCE: 31
tgtaaatatc ggcttctaag                                      20

<210> SEQ ID NO 32
<211> LENGTH: 18
<212> TYPE: DNA
<213> ORGANISM: Artificial
<220> FEATURE:

<223> OTHER INFORMATION: PCR primer

<400> SEQUENCE: 32
ctgaaacaaa tcgcatta                                                                 18

<210> SEQ ID NO 33
<211> LENGTH: 20
<212> TYPE: DNA
<213> ORGANISM: Artificial
<220> FEATURE:
<223> OTHER INFORMATION: PCR primer

<400> SEQUENCE: 33
gttttgggaa gttttgctgg                                                               20

<210> SEQ ID NO 34
<211> LENGTH: 24
<212> TYPE: DNA
<213> ORGANISM: Artificial
<220> FEATURE:
<223> OTHER INFORMATION: PCR primer

<400> SEQUENCE: 34
cagtctaaaa gcgagagtat gatg                                                          24

<210> SEQ ID NO 35
<211> LENGTH: 234
<212> TYPE: PRT
<213> ORGANISM: Oryza sativa

<400> SEQUENCE: 35

Met Pro Glu Val Arg Asn Ser Gly Gly Arg Ala Ala Leu Ala Asp Pro
1               5                   10                  15

Ser Gly Gly Gly Phe Phe Ile Arg Arg Thr Thr Ser Pro Pro Gly Ala
            20                  25                  30

Val Ala Val Lys Pro Leu Ala Arg Arg Ala Leu Pro Pro Thr Ser Asn
        35                  40                  45

Lys Glu Asn Val Pro Pro Ser Trp Ala Val Thr Val Arg Ala Thr Pro
    50                  55                  60

Lys Arg Arg Ser Pro Leu Pro Glu Trp Tyr Pro Arg Ser Pro Leu Arg
65                  70                  75                  80

Asp Ile Thr Ser Val Val Lys Ala Val Glu Arg Lys Ser Arg Leu Gly
                85                  90                  95

Asn Ala Ala Val Arg Gln Gln Ile Gln Leu Ser Glu Asp Ser Ser Arg
            100                 105                 110

Ser Val Asp Pro Ala Thr Pro Val Gln Lys Glu Gly Val Pro Gln
        115                 120                 125

Ser Thr Pro Thr Pro Pro Thr Gln Lys Ala Leu Asp Ala Ala Pro
    130                 135                 140

Cys Pro Gly Ser Thr Gln Ala Val Ala Ser Thr Ser Thr Ala Tyr Leu
145                 150                 155                 160

Ala Glu Gly Lys Pro Lys Ala Ser Ser Ser Pro Ser Asp Cys Ser
            165                 170                 175

Phe Gln Thr Pro Ser Arg Pro Asn Asp Pro Ala Leu Ala Asp Leu Met
        180                 185                 190

Glu Lys Glu Leu Ser Ser Ser Ile Glu Gln Ile Glu Lys Met Val Arg
    195                 200                 205

-continued

```
Lys Asn Leu Lys Arg Ala Pro Lys Ala Ala Gln Pro Ser Lys Val Thr
    210                 215                 220
Ile Gln Lys Arg Thr Leu Leu Ser Met Arg
225                 230
```